(12) United States Patent
Yang

(10) Patent No.: US 11,274,099 B2
(45) Date of Patent: Mar. 15, 2022

(54) DERIVATIVES OF RESIQUIMOD

(71) Applicant: Superb Wisdom Limited, Apia (WS)

(72) Inventor: Lihu Yang, Edison, NJ (US)

(73) Assignee: Superb Wisdom Limited, Apia (WS)

( * ) Notice: Subject to any disclaimer, the term of this patent is extended or adjusted under 35 U.S.C. 154(b) by 0 days.

(21) Appl. No.: 16/612,216

(22) PCT Filed: May 18, 2018

(86) PCT No.: PCT/US2018/033493
§ 371 (c)(1),
(2) Date: Nov. 8, 2019

(87) PCT Pub. No.: WO2018/213769
PCT Pub. Date: Nov. 22, 2018

(65) Prior Publication Data
US 2020/0207757 A1    Jul. 2, 2020

Related U.S. Application Data

(60) Provisional application No. 62/508,722, filed on May 19, 2017.

(51) Int. Cl.
*C07D 471/04* (2006.01)
*A61K 45/06* (2006.01)

(52) U.S. Cl.
CPC ............ *C07D 471/04* (2013.01); *A61K 45/06* (2013.01); *C07B 2200/05* (2013.01)

(58) Field of Classification Search
None
See application file for complete search history.

(56) References Cited

U.S. PATENT DOCUMENTS

| | | | |
|---|---|---|---|
| 4,689,338 A * | 8/1987 | Gerster | C07D 471/04 514/293 |
| 5,389,640 A | 2/1995 | Gerster et al. | |
| 6,221,335 B1 * | 4/2001 | Foster | C07B 59/002 424/1.81 |
| 6,348,462 B1 | 2/2002 | Gerster et al. | |
| 2006/0183767 A1 | 8/2006 | Mandrea | |
| 2011/0104186 A1 | 5/2011 | Valiante et al. | |
| 2020/0207757 A1 | 7/2020 | Yang | |

FOREIGN PATENT DOCUMENTS

WO    WO-92/15582 A1    9/1992

OTHER PUBLICATIONS

Dockrell "Imiquimod and resiquimod as novel immunomodulators" Journal of Antimicrobial and Chemotherapy 2001 48, 751-755.*
Kushner et al., "Pharmacological uses and perspectives of heavy water and deuterated compounds" Canadian Journal of Physiology and Pharmacology, 1999, 77, 79-88.*
Dyck et. al., Journal of Neurochemistry 1986, 46, 399-404.*
Lipka, E. "Evaluation of Imiquimod and analogs with respect to their oral delivery potential" From Proceedings of the International Symposium on Controlled Release of Bioactive Materials (1997), 24th, 337-338 (abstract only).*
Foster, "Deuterium isotope effects in the metabolism of drugs and xenobiotics: implications for drug design," Advances Drug Research 14:1-40 (1985).
International Preliminary Report on Patentability for International Application No. PCT/US2018/033493 dated Nov. 19, 2019.
Jones, "Resiquimod 3M," Curr Op Invest Drugs 4(2):214-218 (2003).
Shao et al., "The kinetic isotope effect in the search for deuterated drugs," Drugs News Pers 23(6):398-404 (2010).
Fisher et al., "The complexities inherent in attempts to decrease drug clearance by blocking sites of CYP-mediated metabolism," Current Opinion in Drug Discovery & Development, 9(1): 101-109 (2006).
Haskins et al., "The Application of Stable Isotopes in Biomedical Research," Biomedical Mass Spectrometry, 9(7): 269-277 (1982).
Tonn et al., "Simultaneous analysis of diphenhydramine and a stable isotope analog (2H10)diphenhydramine using capillary gas chromatography with mass selective detection in biological fluids from chronically instrumented pregnant ewes," Biological Mass Spectrometry, 22(11): 633-642 (1993).
Wolen, "The Application of Stable Isotopes to Studies of Drug Bioavailability and Bioequivalence," J Clin Pharmacol, 26: 419-424 (1986).

* cited by examiner

*Primary Examiner* — David K O'Dell
(74) *Attorney, Agent, or Firm* — Foley Hoag LLP

(57) ABSTRACT

A deuterated compound having structural formula I or a pharmaceutically acceptable salt thereof: Values and example values of the variable in formula (I) are disclosed herein. Also disclosed are the use of compounds of formula (I) in the methods of treating a disease selected from cancer, an autoimmune disease, and an infectious disease, and methods of enhancing an immune response to an antigen.

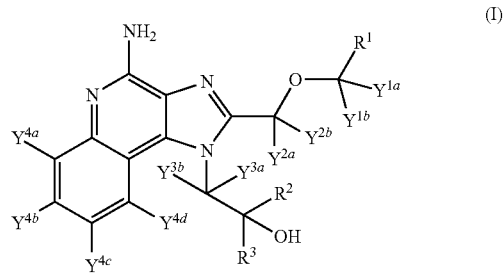

28 Claims, 10 Drawing Sheets

DERIVATIVES OF RESIQUIMOD

RELATED APPLICATION

This application is the U.S. National Stage of International Application No. PCT/US2018/033493, filed May 18, 2018, which designates the U.S., published in English, and claims the benefit of U.S. Provisional Application No. 62/508,722, filed May 19, 2017. The entire teachings of the above applications are incorporated herein by reference.

BACKGROUND

Resiquimod (R-848) is a drug that acts as an immune response modifier, and has antiviral and antitumour activity. It is used as a topical gel in the treatment of skin lesions such as those caused by the herpes simplex virus and cutaneous T-cell lymphoma, and as an adjuvant to increase the effectiveness of vaccines.

As many current medicines, Resiquimod suffers from poor metabolism properties that limit its wider use. One such problem is rapid metabolism that causes it to be cleared too rapidly from the body. While higher dosing may attain a higher plasma level of the drug, it often also causes poor patient compliance, undesirable side effects, and increased cost of treatment. A rapidly metabolized drug may also expose patients to undesirable toxic or reactive metabolites. Despite the beneficial activities of Resiquimod, there is a continuing need for new compounds to treat the diseases and conditions for which Resiquimod is found effective.

SUMMARY OF THE INVENTION

This invention relates to novel derivatives of the imidazoquinolinyl compound Resiquimod (1-(4-Amino-2-(ethoxymethyl)-1H-imidazo[4,5-c]quinolin-1-yl)-2-methyl-propan-2-ol),

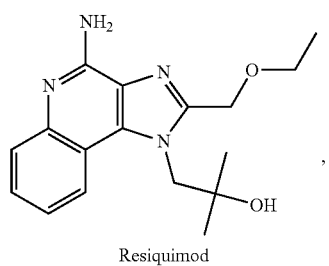 [SMILES: CCOCc1nc2c(N)nc3ccccc3c2n1CC(C)(C)O ; "Resiquimod"]

Resiquimod pharmaceutically acceptable salts, solvates, and hydrates thereof. This invention also provides compositions comprising a compound of this invention and the use of such compositions in methods of treating diseases and conditions that are beneficially treated by administering an agonist of toll-like receptor 7 and 8 (TLR7/TLR8) MyD88-dependent signaling pathway, and/or an upregulator of the opioid growth factor receptor.

In one embodiment, the present invention is a compound having structural formula I:

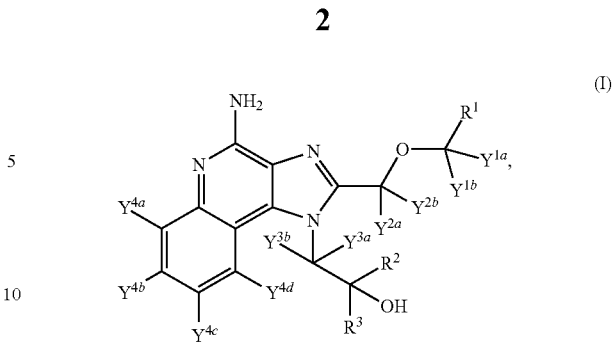

or a pharmaceutically acceptable salt thereof, wherein each of $R^1$, $R^2$ and $R^3$ is independently selected from —$CH_3$, —$CH_2D$, —$CHD_2$, and —$CD_3$; each of $Y^{1a}$, $Y^{1b}$, $Y^{2a}$, $Y^{2b}$, $Y^{3a}$, $Y^{3b}$, $Y^{4a}$, $Y^{4b}$, $Y^{4c}$, and $Y^{4d}$ is independently selected from hydrogen and deuterium; and when each of $R^1$, $R^2$ and $R^3$ is —$CH_3$, at least one of $Y^{1a}$, $Y^{1b}$, $Y^{2a}$, $Y^{2b}$, $Y^{3a}$, $Y^{3b}$, $Y^{4a}$, $Y^{4b}$, $Y^{4c}$, and $Y^{4d}$ is deuterium.

In another embodiment, the present invention is a method of treating a disease selected from cancer, an autoimmune disease, and an infectious disease comprising the step of administering to a subject in need thereof an effective amount of a compound of formula (I).

In another embodiment, the present invention is a method of enhancing an immune response to an antigen in a subject comprising the step of co-administering to the subject the antigen and a compound of a formula (I) in an effective amount.

In another embodiment, the present invention is a method of treating cancer comprising the step of co-administering to a subject in need thereof, an effective amount a compound of formula (I) and a second therapeutic agent selected from an immunotherapy agent and a therapeutic antibody.

In another embodiment, the present invention relates to the use of a compound of formula (I) or a pharmaceutically acceptable salt thereof for treating a disease selected from cancer, an autoimmune disease, and an infectious disease.

In another embodiment, the present invention relates to the use of a compound of formula (I) in the manufacture of a medicament for the treatment of a disease selected from cancer, an autoimmune disease, and an infectious disease.

DETAILED DESCRIPTION

Definitions

Figure 1A:
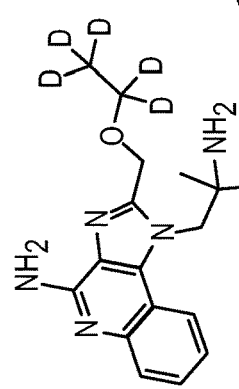
FIGS. 1A-1C, in combination, represent an $^1$H NMR spectrum of compound 107 plotted as signal intensity (vertical axis) vs. chemical shift (in ppm on the horizontal axis). Signal integration also shown.
Figure 1A:
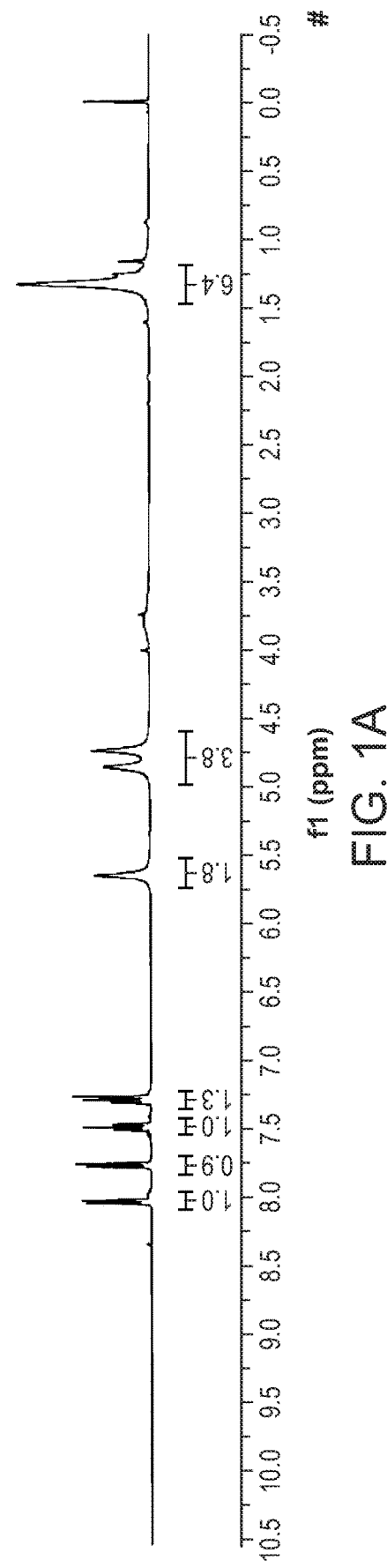

The terms "treat" or ameliorate mean decrease, suppress, attenuate, diminish, arrest, or stabilize the development or progression of a disease (e.g., a disease or disorder delineated herein), lessen the severity of the disease or improve the symptoms associated with the disease.

"Disease" means any condition or disorder that damages or interferes with the normal function of a cell, tissue, or organ.

It will be recognized that some variation of natural isotopic abundance occurs in a synthesized compound depending upon the origin of chemical materials used in the synthesis. Thus, a preparation of resiquimod will inherently contain small amounts of deuterated isotopologues. The concentration of naturally abundant stable hydrogen and carbon isotopes, notwithstanding this variation, is small and immaterial as compared to the degree of stable isotopic substitution of compounds of this invention. See, for instance, Wada, E et al., Seikagaku, 1994, 66: 15; Gannes, L Z et al., Comp Biochem Physiol Mol Integr Physiol, 1998, 119:725.

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Also unless otherwise stated, when a position is designated specifically as "D" or "deuterium", the position is understood to have deuterium at an abundance that is at least 3340 times greater than the natural abundance of deuterium, which is 0.015% (i.e., at least 50.1% incorporation of deuterium).

The term "isotopic enrichment factor" as used herein means the ratio between the isotopic abundance and the natural abundance of a specified isotope.

In various embodiments, compounds of this invention have an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

The term "isotopologue" refers to a species that differs from a specific compound of this invention only in the isotopic composition thereof.

The term "compound," when referring to a compound of this invention, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound. However, as set forth above the relative amount of such isotopologues in toto will be less than 49.9% of the compound. In other embodiments, the relative amount of such isotopologues in toto will be less than 47.5%, less than 40%, less than 32.5%, less than 25%, less than 17.5%, less than 10%, less than 5%, less than 3%, less than 1%, or less than 0.5% of the compound.

The invention also provides salts, solvates or hydrates of the compounds of the invention.

A salt of a compound of this invention can be formed, for example, between a basic group of the compound, such as an amino functional group. According to another embodiment, the compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

As used herein, the term "hydrate" means a compound which further includes a stoichiometric or non-stoichiometric amount of water bound by non-covalent intermolecular forces.

As used herein, the term "solvate" means a compound which further includes a stoichiometric or non-stoichiometric amount of solvent such as water, acetone, ethanol, methanol, dichloromethane, 2-propanol, or the like, bound by non-covalent intermolecular forces.

The compounds of the present invention (e.g., a deuterated resiquimod), may contain an asymmetric carbon atom, for example, as the result of deuterium substitution or otherwise. As such, compounds of this invention can exist as either individual enantiomers, or mixtures of the two enantiomers. Accordingly, a compound of the present invention may exist as either a racemic mixture or a scalemic mixture, or as individual respective stereoisomers that are substantially free from another possible stereoisomer. The term "substantially free of other stereoisomers" as used herein means less than 25% of other stereoisomers, preferably less than 10% of other stereoisomers, more preferably less than 5% of other stereoisomers and most preferably less than 2% of other stereoisomers are present. Methods of obtaining or synthesizing an individual enantiomer for a given compound are known in the art and may be applied as practicable to final compounds or to starting material or intermediates.

Unless otherwise indicated, when a disclosed compound is named or depicted by a structure without specifying the stereochemistry and has one or more chiral centers, it is understood to represent all possible stereoisomers of the compound.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" and "d" both refer to deuterium. "Stereoisomer" refers to both enantiomers and diastereomers. "Tert", "ᵗ", and "t-" each refer to tertiary. "US" refers to the United States of America.

"Substituted with deuterium" refers to the replacement of one or more hydrogen atoms with a corresponding number of deuterium atoms.

Throughout this specification, a variable may be referred to generally (e.g., "each R") or may be referred to specifically (e.g., $R^1$, $R^2$, $R^3$, etc.). Unless otherwise indicated, when a variable is referred to generally, it is meant to include all specific embodiments of that particular variable.

Therapeutic Compounds

In a first embodiment, the present invention provides a compound of Formula

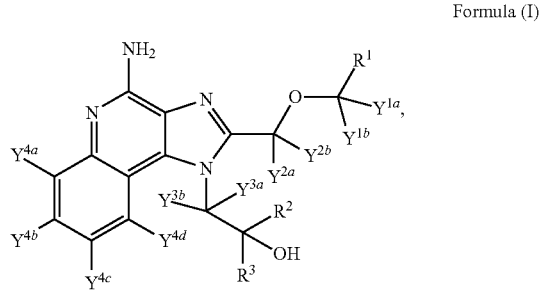

Formula (I)

or a pharmaceutically acceptable salt thereof. In formula (I), each of $R^1$, $R^2$ and $R^3$ is independently selected from —CH$_3$, —CH$_2$D, —CHD$_2$, and —CD$_3$; each of $Y^{1a}$, $Y^{1b}$, $Y^{2a}$, $Y^{2b}$, $Y^{3a}$, $Y^{3b}$, $Y^{4a}$, $Y^{4b}$, $Y^{4c}$, and $Y^{4d}$ is independently selected from hydrogen and deuterium; and when each of $R^1$, $R^2$ and $R^3$ is —CH$_3$, at least one of $Y^{1a}$, $Y^{1b}$, $Y^{2a}$, $Y^{2b}$, $Y^{3a}$, $Y^{3b}$, $Y^{4a}$, $Y^{4b}$, $Y^{4c}$, and $Y^{4d}$ is deuterium.

In a first aspect of the first embodiment, each of $R^1$, $R^2$ and $R^3$ is independently selected from —CH$_3$ and —CD$_3$. The remainder of the values and the example values of the variables in formula (I) are as described above and below with respect to various aspects of the first embodiment.

In a second aspect of the first embodiment, $Y^{1a}$ and $Y^{1b}$ are the same; $Y^{2a}$ and $Y^{2b}$ are the same; $Y^{3a}$ and $Y^{3b}$ are the same; and $Y^{4a}$, $Y^{4b}$, $Y^{4c}$, and $Y^{4d}$ are the same. The remainder of the values and the example values of the variables in formula (I) are as described above and below with respect to various aspects of the first embodiment.

In a third aspect of the first embodiment, each of $Y^{4a}$, $Y^{4b}$, $Y^{4c}$, and $Y^{4d}$ is hydrogen. The remainder of the values and the example values of the variables in formula (I) are as described above and below with respect to various aspects of the first embodiment.

In a fourth aspect of the first embodiment, each of $Y^{4a}$, $Y^{4b}$, $Y^{4c}$, and $Y^{4d}$ is deuterium. The remainder of the values and the example values of the variables in formula (I) are as described above and below with respect to various aspects of the first embodiment.

In a fifth aspect of the first embodiment, each of $Y^{1a}$ and $Y^{1b}$ is deuterium. The remainder of the values and the example values of the variables in formula (I) are as described above and below with respect to various aspects of the first embodiment.

In a sixth aspect of the first embodiment, each of $Y^{1a}$ and $Y^{1b}$ is hydrogen. The remainder of the values and the example values of the variables in formula (I) are as described above and below with respect to various aspects of the first embodiment.

In a seventh aspect of the first embodiment, each of $Y^{2a}$ and $Y^{2b}$ is deuterium. The remainder of the values and the example values of the variables in formula (I) are as described above and below with respect to various aspects of the first embodiment.

In an eighth aspect of the first embodiment, each of $Y^{2a}$ and $Y^{2b}$ is hydrogen. The remainder of the values and the example values of the variables in formula (I) are as described above and below with respect to various aspects of the first embodiment.

In a ninth aspect of the first embodiment, each of $Y^3a$ and $Y^{3b}$ is deuterium. The remainder of the values and the example values of the variables in formula (I) are as described above and below with respect to various aspects of the first embodiment.

In a tenth aspect of the first embodiment, each of $Y^{3a}$ and $Y^{3b}$ is hydrogen. The remainder of the values and the example values of the variables in formula (I) are as described above and below with respect to various aspects of the first embodiment.

In an eleventh aspect of the first embodiment, $R^1$ is —CD$_3$. The remainder of the values and the example values of the variables in formula (I) are as described above and below with respect to various aspects of the first embodiment.

In a twelfth aspect of the first embodiment, $R^1$ is —CH$_3$. The remainder of the values and the example values of the variables in formula (I) are as described above and below with respect to various aspects of the first embodiment.

In a thirteenth aspect of the first embodiment, each of $R^2$ and $R^3$ is —CD$_3$. The remainder of the values and the example values of the variables in formula (I) are as described above and below with respect to various aspects of the first embodiment.

In a fourteenth aspect of the first embodiment, each of $R^2$ and $R^3$ is —CH$_3$. The remainder of the values and the example values of the variables in formula (I) are as described above and below with respect to various aspects of the first embodiment.

In a fifteenth aspect of the first embodiment, any atom not designated as deuterium or D in formula (I) is present at its natural isotopic abundance.

In a sixteenth aspect of the first embodiment, each of $Y^{4a}$, $Y^{4b}$, $Y^{4c}$, and $Y^{4d}$ is hydrogen; $Y^{1a}$ and $Y^{1b}$ are the same; $Y^{2a}$ and $Y^{2b}$ are the same; $Y^{3a}$ and $Y^{3b}$ are the same; and $R^2$ and $R^3$ are the same. The remainder of the values and the example values of the variables in formula (I) are as described above and below with respect to various aspects of the first embodiment.

In the seventeenth aspect of the first embodiment, each of $Y^{4a}$, $Y^{4b}$, $Y^{4c}$, and $Y^{4d}$ is hydrogen; $Y^{1a}$ and $Y^{1b}$ are the same; $Y^{2a}$ and $Y^{2b}$ are the same; $Y^{3a}$ and $Y^{3b}$ are the same; and $R^2$ and $R^3$ are the same; and the values of $Y^{2a}$, $Y^{2b}$, $Y^{3a}$, $Y^{3b}$, $R^1$, $R^2$ and $R^3$ are selected from the values listed in Table 1, below:

TABLE 1

| Compound | $Y^{1a}/Y^{1b}$ | $Y^{2a}/Y^{2b}$ | $Y^{3a}/Y^{3b}$ | $R^1$ | $R^2/R^3$ |
|---|---|---|---|---|---|
| 100 | D | H | H | CH₃ | CH₃ |
| 101 | H | D | H | CH₃ | CH₃ |
| 102 | H | H | D | CH₃ | CH₃ |
| 103 | H | H | H | CD₃ | CH₃ |
| 104 | H | H | H | CH₃ | CD₃ |
| 105 | D | D | H | CH₃ | CH₃ |
| 106 | D | H | D | CH₃ | CH₃ |
| 107 | D | H | H | CD₃ | CH₃ |
| 108 | D | H | H | CH₃ | CD₃ |
| 109 | H | D | D | CH₃ | CH₃ |
| 110 | H | D | H | CD₃ | CH₃ |
| 111 | H | D | H | CH₃ | CD₃ |
| 112 | H | H | D | CD₃ | CH₃ |
| 113 | H | H | D | CH₃ | CD₃ |
| 114 | H | H | H | CD₃ | CD₃ |
| 115 | D | D | D | CH₃ | CH₃ |
| 116 | D | D | H | CD₃ | CH₃ |
| 117 | D | D | H | CH₃ | CD₃ |
| 118 | D | H | D | CD₃ | CH₃ |
| 119 | D | H | D | CH₃ | CD₃ |
| 120 | D | H | H | CD₃ | CD₃ |
| 121 | H | D | D | CD₃ | CH₃ |
| 122 | H | D | D | CH₃ | CD₃ |
| 123 | H | D | H | CD₃ | CD₃ |
| 124 | H | H | D | CD₃ | CD₃ |
| 125 | D | D | D | CD₃ | CH₃ |
| 126 | D | D | D | CH₃ | CD₃ |
| 127 | D | D | H | CD₃ | CD₃ |
| 128 | D | H | D | CD₃ | CD₃ |
| 129 | H | D | D | CD₃ | CD₃ |
| 130 | D | D | D | CD₃ | CD₃ |

For the compounds defined by the values of the variables of formula (I) listed in Table 1, any atom not designated as deuterium or D is present at its natural isotopic abundance.

In the eighteenth aspect of the first embodiment, each of $Y^{4a}$, $Y^{4b}$, $Y^{4c}$, and $Y^{4d}$ is deuterium; $Y^{1a}$ and $Y^{1b}$ are the same; $Y^{2a}$ and $Y^{2b}$ are the same; $Y^{3a}$ and $Y^{3b}$ are the same; and $R^2$ and $R^3$ are the same. The remainder of the values and the example values of the variables of formula (1) are as described above and below with respect to various aspects of the first embodiment.

In the nineteenth aspect of the first embodiment, each of $Y^{4a}$, $Y^{4b}$, $Y^{4c}$, and $Y^{4d}$ is deuterium; $Y^{1a}$ and $Y^{1b}$ are the same; $Y^{2a}$ and $Y^{2b}$ are the same; $Y^{3a}$ and $Y^{3b}$ are the same; and $R^2$ and $R^3$ are the same; and the values of $Y^{2a}$, $Y^{2b}$, $Y^{3a}$, $Y^{3b}$, $R^1$, $R^2$ and $R^3$ are selected from the values listed in Table 2, below:

TABLE 2

| Compound | $Y^{1a}/Y^{1b}$ | $Y^{2a}/Y^{2b}$ | $Y^{3a}/Y^{3b}$ | $R^1$ | $R^2/R^3$ |
|---|---|---|---|---|---|
| 131 | D | H | H | CH₃ | CH₃ |
| 132 | H | D | H | CH₃ | CH₃ |
| 133 | H | H | D | CH₃ | CH₃ |
| 134 | H | H | H | CD₃ | CH₃ |
| 135 | H | H | H | CH₃ | CD₃ |
| 136 | D | D | H | CH₃ | CH₃ |
| 137 | D | H | D | CH₃ | CH₃ |
| 138 | D | H | H | CD₃ | CH₃ |
| 139 | D | H | H | CH₃ | CD₃ |
| 140 | H | D | D | CH₃ | CH₃ |
| 141 | H | D | H | CD₃ | CH₃ |
| 142 | H | D | H | CH₃ | CD₃ |
| 143 | H | H | D | CD₃ | CH₃ |
| 144 | H | H | D | CH₃ | CD₃ |
| 145 | H | H | H | CD₃ | CD₃ |
| 146 | D | D | D | CH₃ | CH₃ |
| 147 | D | D | H | CD₃ | CH₃ |
| 148 | D | D | H | CH₃ | CD₃ |
| 149 | D | H | D | CD₃ | CH₃ |
| 150 | D | H | D | CH₃ | CD₃ |
| 151 | D | H | H | CD₃ | CD₃ |
| 152 | H | D | D | CD₃ | CH₃ |
| 153 | H | D | D | CH₃ | CD₃ |
| 154 | H | D | H | CD₃ | CD₃ |
| 155 | H | H | D | CD₃ | CD₃ |
| 156 | D | D | D | CD₃ | CH₃ |
| 157 | D | D | D | CH₃ | CD₃ |
| 158 | D | D | H | CD₃ | CD₃ |
| 159 | D | H | D | CD₃ | CD₃ |
| 160 | H | D | D | CD₃ | CD₃ |
| 161 | D | D | D | CD₃ | CD₃ |
| 162 | H | H | H | CH₃ | CH₃ |

For the compounds defined by the values of the variables of formula (I) listed in Table 2, any atom not designated as deuterium or D is present at its natural isotopic abundance.

In a twentieth aspect of the first embodiment, the compound is selected from:

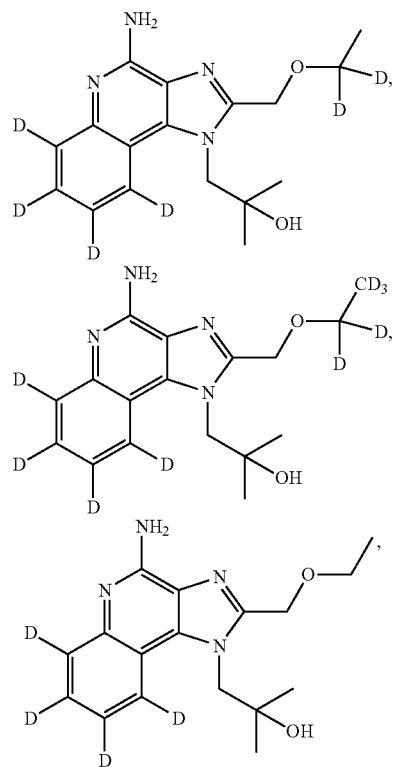

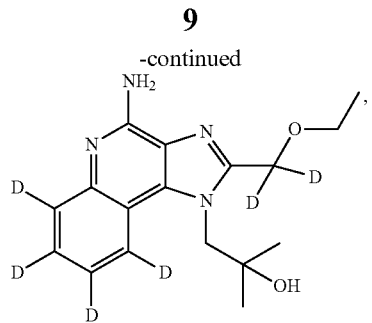
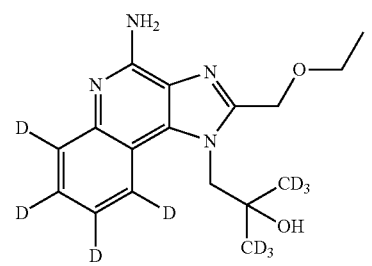
or a pharmaceutically acceptable salt thereof.
In the twenty-first aspect of the first embodiment, the compound is selected
(Compound 107)
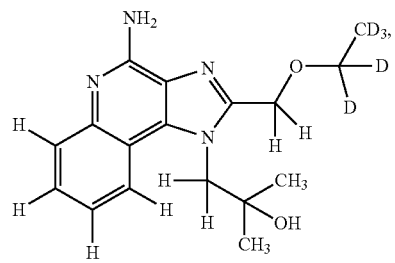
(Compound 100)
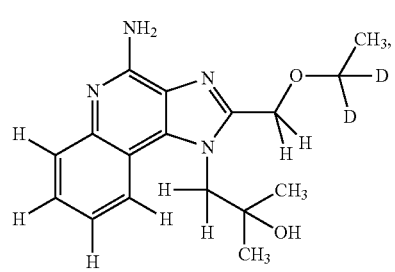
(Compound 101)
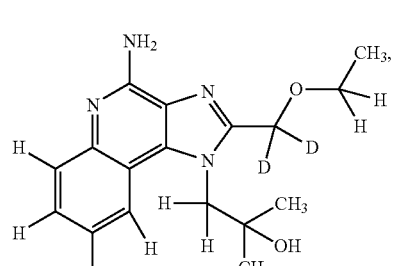
(Compound 104)
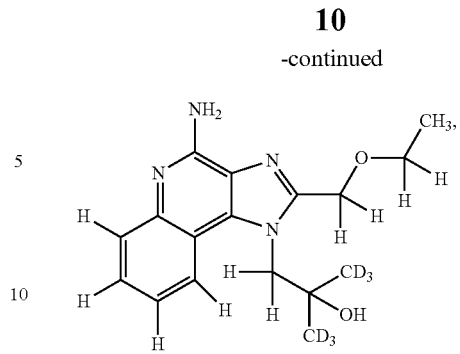
(Compound 113)
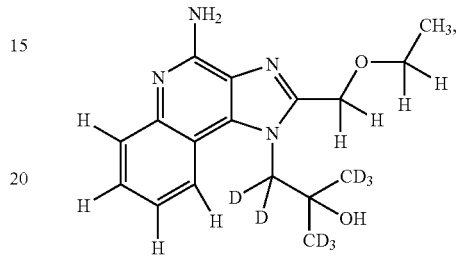
(Compound 116)
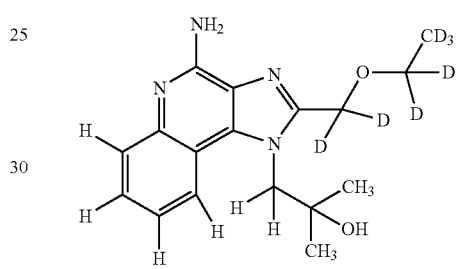
(Compound 105)
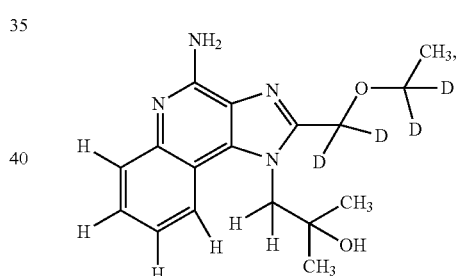
(Compound 131)
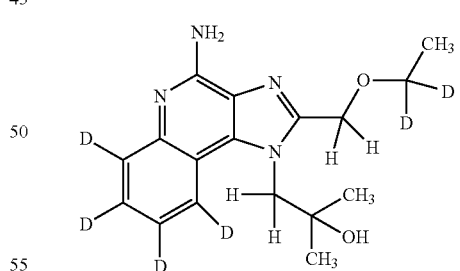
(Compound 138)
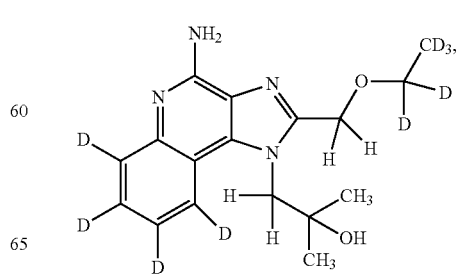

(Compound 162)
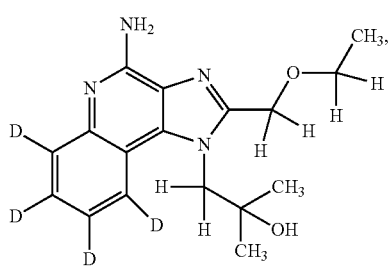
(Compound 132)
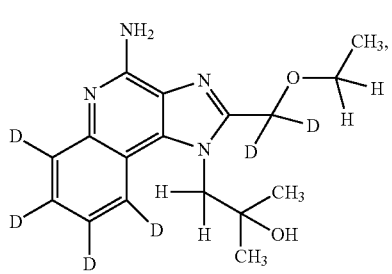
(Compound 136)
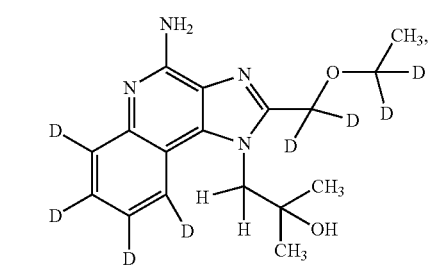
(Compound 137)
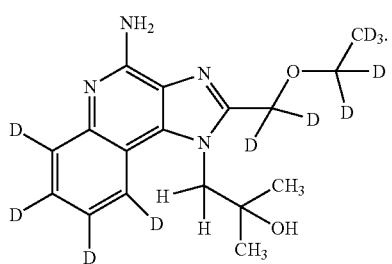
In a twenty-second aspect of the first embodiment, the compound is selected from:
(Compound 107)
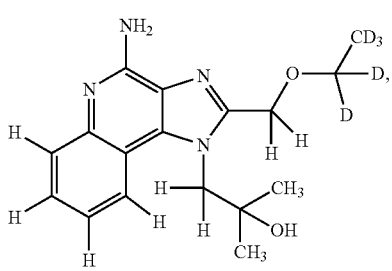
(Compound 100)
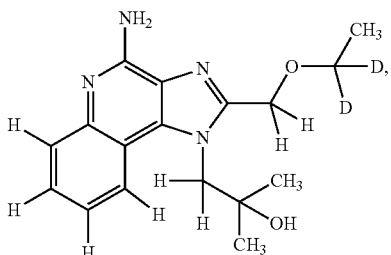
(Compound 101)
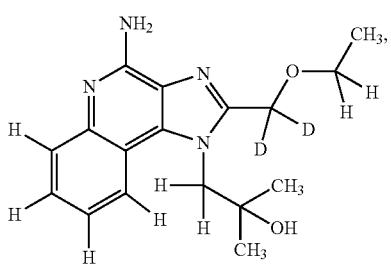
(Compound 104)
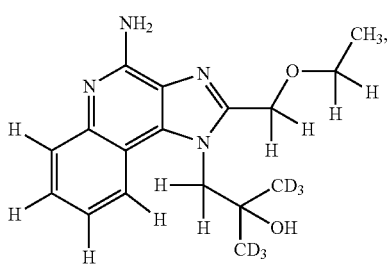
(Compound 113)
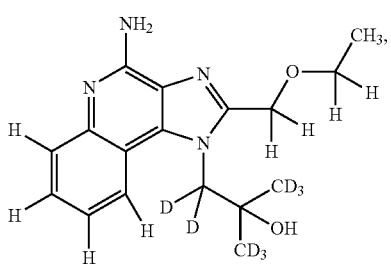
(Compound 105)
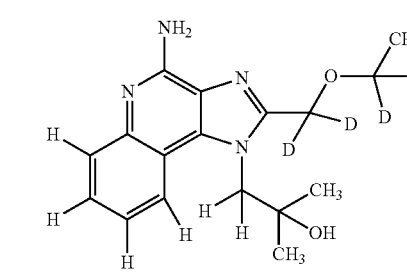

-continued (Compound 116)

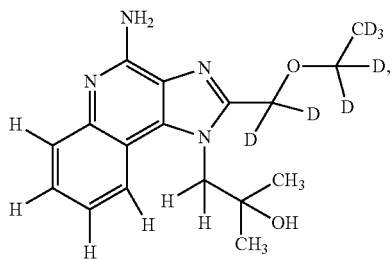

or a pharmaceutically acceptable salt thereof.

In a second embodiment, the present invention provides a compound of Formula I represented by Formula 1a:

i.

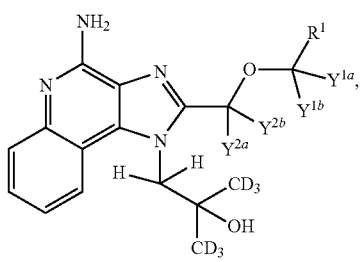

or a pharmaceutically acceptable salt thereof, wherein: $R^1$ is selected from —$CH_3$, and —$CD_3$; $Y^{1a}$ and $Y^{1b}$ are the same and selected from hydrogen and deuterium; and $Y^{2a}$ and $Y^{2b}$ are the same and are selected from hydrogen and deuterium.

In a first aspect of the second embodiment $Y^{2a}$ and $Y^{2b}$ are the hydrogen. The remainder of the values and the example values of the variable in formula (Ia) are as described above and below with respect to various aspects of the second embodiment.

In a second aspect of the second embodiment, $R^1$ is —$CD_3$ and each of $Y^{1a}$ and $Y^{1b}$ is deuterium. The remainder of the values and the example values of the variable in formula (Ia) are as described above and below with respect to various aspects of the second embodiment.

In a third aspect of the second embodiment, $R^1$ is —$CH_3$ and each of $Y^{1a}$ and $Y^{1b}$ is hydrogen. The remainder of the values and the example values of the variable in formula (Ia) are as described above and below with respect to various aspects of the second embodiment.

In a fourth aspect of the second embodiment, the compound is represented by the following structural formula:

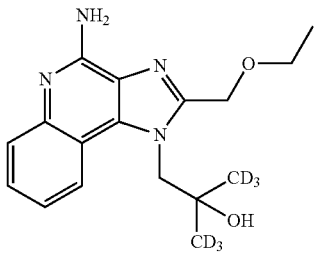 [SMILES: [2H]C([2H])([2H])C(O)(Cn1c(COCC)nc2c(N)nc3ccccc3c21)C([2H])([2H])[2H]]

or a pharmaceutically acceptable salt thereof.

In a third embodiment, the present invention provides a compound of Formula I represented by Formula 1b:

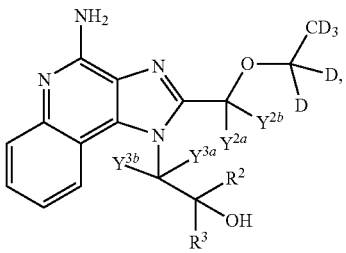

or a pharmaceutically acceptable salt thereof, wherein: each of $R^2$ and $R^3$ is independently selected from —$CH_3$ and —$CD_3$; $Y^{2a}$ and $Y^{2b}$ are the same and selected from hydrogen and deuterium; and $Y^{3a}$ and $Y^{3b}$ are the same and are selected from hydrogen and deuterium.

In a first aspect of the third embodiment $Y^{2a}$ and $Y^{2b}$ are the hydrogen. The remainder of the values and the example values of the variable in formula (Ib) are as described above and below with respect to various aspects of the third embodiment.

In a second aspect of the third embodiment $Y^{3a}$ and $Y^{3b}$ are the hydrogen. The remainder of the values and the example values of the variable in formula (Ib) are as described above and below with respect to various aspects of the third embodiment.

In a third aspect of the third embodiment $R^2$ and $R^3$ are the same. The remainder of the values and the example values of the variable in formula (Ib) are as described above and below with respect to various aspects of the third embodiment.

In a fourth aspect of the third embodiment $R^2$ and $R^3$ are —$CH_3$. The remainder of the values and the example values of the variable in formula (Ib) are as described above and below with respect to various aspects of the third embodiment.

In a fifth aspect of the third embodiment $R^2$ and $R^3$ are —$CD_3$. The remainder of the values and the example values of the variable in formula (Ib) are as described above and below with respect to various aspects of the third embodiment.

In a sixth aspect of the third embodiment, the compound is represented by the following structural formula:

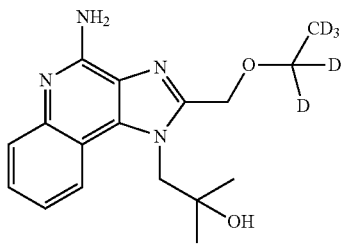 [SMILES: [2H]C([2H])([2H])C([2H])([2H])OCc1nc2c(N)nc3ccccc3c2n1CC(C)(C)O]

or a pharmaceutically acceptable salt thereof.

In various aspects of the first, second and third embodiments, any atom not designated as deuterium in any of the recited aspects is present at its natural isotopic abundance.

In various aspects of the first, second and third embodiments, any atom designated as deuterium in any of the recited aspects is present in at least 90%, at least 95%, or at least 99% isotopic abundance.

In a fourth embodiment, the present invention is a pharmaceutical composition comprising a compound of any one of the aspects of the first, second and third embodiments set forth above, and a pharmaceutically acceptable carrier.

In a fifth embodiment, the present invention is a method of treating a disease selected from cancer, an autoimmune disease, and an infectious disease comprising the step of administering to a subject in need thereof an effective amount of a compound of any one of the aspects of the first, second and third embodiments, or a pharmaceutical composition of the fourth embodiment.

Examples of cancers include melanoma (including recurrent melanoma, metastatic melanoma, and mucosal melanoma), cutaneous T-cell lymphoma, Nodular Basal Cell Carcinoma, Glioma, Anaplastic Astrocytoma, Anaplastic Astro-oligodendroglioma, Glioblastoma, and bladder cancer.

Examples of autoimmune diseases include rheumatoid arthritis, lupus, celiac disease, Sjögren's syndrome, polymyalgia rheumatic, multiple sclerosis, ankylosing spondylitis, Type 1 diabetes, alopecia areata, vasculitis, and temporal arteritis.

Examples of infectious diseases include warts, influenza infection, tuberculosis, Hepatitis B, common cold, streptococcal infections, urinary tract infections, pneumonia, sexually transmitted diseases, HIV, and malaria.

In one aspect of the fifth embodiment, the disease is cutaneous T-cell lymphoma.

In a sixth embodiment, the present invention is a method of enhancing an immune response to an antigen in a subject comprising the step of co-administering to the subject the antigen and a compound of any one of the aspects of the first, second and third embodiments, or a pharmaceutical composition of the fourth embodiment in an effective amount.

In a first aspect of the sixth embodiment, the antigen is selected from a cancer antigen, an influenza antigen, a Hepatitis B virus antigen. As used herein, the term "cancer antigen" refers to a protein or carbohydrate that is either expressed by cancerous cells but not by healthy cells or is expressed by cancerous cells in much greater concentrations than by healthy cells. Examples of tumor antigens include Alpha-fetoprotein (AFP) of Nonseminomatous germ cell tumor, CA 15-3 of Breast cancer, CA 19-9 of Pancreatic cancer, CA 50 of Gastrointestinal tract tumors, CA 125 of Ovarian/peritoneal cancer, Carcinoembryonic antigen (CEA) of Gastrointestinal tract tumors and tumors of solid internal organs, Human chorionic gonadotropin (HCG) of Nonseminomatous germ cell tumors and choriocarcinoma, Microglobulin-beta 2 subunit (b2-M) of Multiple myeloma, Neuron-specific enolase (NSE) of small cell carcinoma of lung, NY-BR-40 of Breast cancer, Prostate specific antigen (PSA) Prostate cancer, Urinary tumor associated antigen (UTAA) of Melanoma, NY-ESO-1 family of the cancer/testis family, glycoprotein 100 (gp100) of melanoma, Melanoma-associated antigen 3 (MAGE-A3), CDX-1401 (a fully human monoclonal antibody with specificity for the dendritic cell receptor DEC-205 linked to the NY-ESO-1 tumor antigen), long peptide vaccine 7 (LPV7, a peptide vaccine consisting of a combination of seven synthetic long peptides (SLPs), which are each about 30 amino acids in size, and derived from cancer-testis antigens (CTA) and melanocytic differentiation proteins (MDP)), autologous tumor lysate, and others.

In a second aspect of the sixth embodiment, the cancer antigen is selected from NY-ESO-1 protein, NY-ESO-1b peptide, gp100, MAGE-3, CDX-1401, LPV7, and an autologous tumor lysate.

In a seventh embodiment, the present invention is a method of treating cancer comprising the step of co-administering to a subject in need thereof an effective amount, a compound of any one of the aspects of the first, second and third embodiments, or a pharmaceutical composition of the fourth embodiment; and a second therapeutic agent or more than one second therapeutic agents selected from an immunotherapy agent and a therapeutic antibody.

Examples of immunotherapy agents include Interleukins (IL-2, IL-7, IL-12), Cytokines (Interferons, G-CSF, Imiquimod), Chemokines (CCL3, CCL26, CXCL7), Immunomodulatory imide drugs (IMiDs, such as thalidomide and its analogues lenalidomide, pomalidomide, and ampremilast), cytosine phosphate-guanosine, oligodeoxynucleotides, and glucans. Immunotherapy agents also include checkpoint inhibitors.

As used herein, a "checkpoint inhibitor" refers to an agent that blocks certain proteins made by some types of immune system cells, such as T cells, and some cancer cells. These proteins help keep immune responses in check and can keep T cells from killing cancer cells. When these proteins are blocked, the "brakes" on the immune system are released and T cells are able to kill cancer cells better. Examples of checkpoint proteins found on T cells or cancer cells include PD-1/PD-L1 and CTLA-4/B7-1/B7-2.

Examples of checkpoint inhibitors include PD-1 inhibitors Pembrolizumab (Keytruda), Nivolumab (Opdivo); PD-L1 inhibitors Atezolizumab (Tecentriq), Avelumab (Bavencio); and CTLA-4 inhibitor: Ipilimumab (Yervoy).

In a first aspect of the seventh embodiment, the immunotherapy agent is a checkpoint inhibitor.

In a second aspect of the seventh embodiment, the immunotherapy agent is an agent that stimulates anticancer immunity. Such agents include CD40 agonistic agents and OX40 agonistic agents. Examples of CD40 agonistic agents include CD40 agonist antibodies (e.g., a monoclonal antibody). Specific CD40 agonistic agents include APX005M, CP-870,893 (Pfizer), Dacetuzmumab (Seattle Genetics) and Chi Lob 7/4 (Univ. of Southampton). Examples of OX40 agonistic agents include OX40 agonistic antibodies (e.g., monoclonal antibodies). Specific OX40 agonistic agents include MED 16469 (MedImmune), MED 16383 (MedImmune), MED 10562 (MedImmune), PF-04518600 (Pfizer), MOXR0916 (Genentech), GSK3174998 (GlaxoSmithKline) and INCAGN01949 (Agenux/Incyte).

In a third aspect of the seventh embodiment, the method of treating cancer comprises the step of co-administering to a subject in need thereof an effective amount, a compound of any one of the aspects of the first, second and third embodiments, or a pharmaceutical composition of the fourth embodiment; and an immunotherapy agent selected from a checkpoint inhibitor, a CD-40 agonistic antibody, an OX-40 agonistic antibody or a combination thereof. For example, an effective amount of a compound of any one of the aspects of the first, second and third embodiments, or a pharmaceutical composition of the fourth embodiment can be administered in combination with a checkpoint inhibitor and a CD-40 agonistic antibody. In another example, an effective amount of a compound of any one of the aspects of the first, second and third embodiments, or a pharmaceutical composition of the fourth embodiment can be administered in combination with a checkpoint inhibitor and an OX-40 agonist antibody.

In a fourth aspect of the seventh embodiment, the therapeutic antibody is selected from an antibody selective for EGFR and an antibody selective for Her 2.

As used herein, "EGFR" refers to the epidermal growth factor receptor (EGFR; ErbB-1; HER1 in humans), a transmembrane protein that is a receptor for members of the epidermal growth factor family (EGF family) of extracellular protein ligands. Examples of antibodies selective for EGFR include Cetuximab (Erbitux), Depatuxizumab mafodotin, Futuximabfor, Imgatuzumab, Laprituximab emtansine, Matuzumab, Necitumumab, Nimotuzumab (Theracim, Theraloc), Panitumumab (Vectibix), and Zalutumumab.

As used herein, "Her 2" refers to human epidermal growth factor receptor 2, also known as receptor tyrosine-protein kinase erbB-2, CD340 (cluster of differentiation 340), proto-oncogene Neu, Erbb2 (rodent), or ERBB2 (human). It is a protein that in humans is encoded by the ERBB2 gene, and is a member of the human epidermal growth factor receptor (HER/EGFR/ERBB) family. Examples of antibodies selective for Her 2 include Trastuzumab (Herceptin), Pertuzumab (Perjeta), and Ado-trastuzumab emtansine (Kadcyla, also known as TDM-1).

The synthesis of compounds of Formula I can be readily achieved by synthetic chemists of ordinary skill. Relevant procedures and intermediates are disclosed, for instance in U.S. Pat. Nos. 5,389,640; 6,200,592; 6,245,776; 6,348,462; and 6,486,168, the relevant teachings of which are incorporated herein by reference.

Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure.

Compositions

The invention also provides pharmaceutical compositions comprising an effective amount of a compound of Formula I (e.g., including any of the formulae herein), or a pharmaceutically acceptable salt, solvate, or hydrate of said compound; and a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this invention optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae described herein is administered intraruorally. In certain embodiments, the compound of the formulae described herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington's Pharmaceutical Sciences, Mack Publishing Company, Philadelphia, Pa. (17th ed. 1985).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention can be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g.: Rabinowitz J D and Zaffaroni A C, U.S. Pat. No. 6,803,031, assigned to Alexza Molecular Delivery Corporation.

The pharmaceutical compositions of this invention can be administered in a liposomal formulation.

Topical administration of the pharmaceutical compositions of this invention is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

In another embodiment, a composition of this invention further comprises a second therapeutic agent. The second therapeutic agent may be selected from any compound or therapeutic agent known to have or that demonstrates advantageous properties when administered with a compound having the same mechanism of action as compounds of formula (I). Such agents include those indicated as being useful in combination with resiquimod, including but not limited to, NY-ESO-1 protein, Montanide ISA®-51 VG, CDX-1401, poly-ICLC (a complex of carboxymethylcellulose, polyinosinic-polycytidylic acid, and poly-L-lysine double-stranded RNA), LPV7, Tetanus peptide (tetanus toxoid helper peptide QYIKANSKFIGITEL), autologous tumor lysate, CDX-1307 (a human monoclonal antibody targeting the mannose receptor, fused to the human chorionic gonadotropin-β chain (hCG-β), a tumor antigen frequently expressed by epithelial cancers including bladder cancer), and other chemotherapeutic agents.

In another embodiment, the invention provides separate dosage forms of a compound of this invention and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to treat (therapeutically or prophylactically) the target disorder. For example, to reduce or ameliorate the severity, duration or progression of the disorder being treated, prevent the advancement of the disorder being treated, cause the regression of the disorder being treated, or enhance or improve the prophylactic or therapeutic effect(s) of another therapy.

The interrelationship of dosages for animals and humans (based on milligrams per meter squared of body surface) is described in Freireich et al., (1966) Cancer Chemother. Rep 50: 219. Body surface area may be approximately determined from height and weight of the patient. See, e.g., Scientific Tables, Geigy Pharmaceuticals, Ardsley, N.Y., 1970, 537.

In one embodiment, an effective amount of a compound of this invention can range from about 0.1 mg to about 500 mg/day. In more specific aspects of this embodiments, an effective amount of a compound of this invention ranges from about 1.0 mg-400 mg/day, from about 5 mg-300 mg/day, from about 10 mg-250 mg/day, from about 20 mg-200 mg/day, from about 50 mg-200 mg/day and from about 100 mg-200 mg/day. Effective dosage amounts may be administered as a single dose once a day, or as split doses administered two, three or four times a day, e.g., 50 mg once per day, or 25 mg twice per day; 100 mg once per day, or 50 mg twice per day; or 200 mg once per day, or 100 mg twice per day.

Effective doses will also vary, as recognized by those skilled in the art, depending on the diseases treated, the severity of the disease, the route of administration, the sex, age and general health condition of the patient, excipient usage, the possibility of co-usage with other therapeutic treatments such as use of other agents and the judgment of the treating physician. For example, guidance for selecting an effective dose can be determined by reference to the prescribing information for a compound of formula (I).

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

It is expected that some of the second therapeutic agents referenced above will act synergistically with the compounds of this invention. When this occurs, it will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

The invention provides a method of treating a disease that is beneficially treated by resiquimod in a patient in need thereof, comprising the step of administering to the patient an effective amount of a compound or a composition of this invention. Such diseases include, but are not limited to, tumors, such as melanoma (recurrent, metastatic or mucosal), cutaneous T-Cell Lymphoma, nodular basal cell carcinoma, glioma, anaplastic astrocytoma, anaplastic astro-oligodendroglioma, glioblastoma, bladder cancer, and mycosis fungoides; actinic keratosis; warts; allergies, including allergic rhinitis and asthma; tuberculosis (including latent); hepatitis B; influenza and other advanced malignancies.

Compounds disclosed herein can also be administered as an enhancer or an adjuvant during influenza vaccination, Identifying a patient in need of such treatment can be in the judgment of a patient or a health care professional and can be subjective (e.g. opinion) or objective (e.g. measurable by a test or diagnostic method).

In another embodiment, any of the above methods of treatment comprises the further step of co-administering to the patient in need thereof one or more second therapeutic agents. The choice of second therapeutic agent may be made from any second therapeutic agent known to be useful for co-administration with the compounds of the present invention. The choice of second therapeutic agent is also dependent upon the particular disease or condition to be treated. Examples of second therapeutic agents that may be employed in the methods of this invention are those set forth above for use in combination compositions comprising a compound of this invention and a second therapeutic agent.

In particular, the combination therapies of this invention include co-administering a compound of Formula I and a second therapeutic agent to a patient in need thereof for treatment of the following conditions (with the particular second therapeutic agent indicated in parentheses following the indication): tumors (NY-ESO-1 protein; Montanide ISA 51 VG); recurrent melanoma; stage IIA melanoma; stage IIB melanoma; stage IIC melanoma; stage IIIA melanoma; stage IIIB melanoma; stage IIIC melanoma; stage IV melanoma (Montanide ISA 51 VG); melanoma (gp100); advanced malignancies (CDX-1401 and/or Poly-ICLC); melanoma; metastatic melanoma; mucosal melanoma (Peptide Vaccine (LPV7) in combination with Tetanus peptide and/or PolyI-CLC); glioma; anaplastic astrocytoma; anaplastic astro-oligodendroglioma; glioblastoma (autologous tumor lysate-pulsed DC vaccination); bladder cancer (CDX-1307); allergies (phthalate).

The term "co-administered" as used herein means that the second therapeutic agent may be administered together with a compound of this invention as part of a single dosage form (such as a composition of this invention comprising a compound of the invention and a second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention, comprising both a compound of the invention and a second therapeutic agent, to a patient does not preclude the separate administration of that same therapeutic agent, any other second therapeutic agent or any compound of this invention to said patient at another time during a course of treatment.

In one embodiment of the invention, where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of a compound of Formula I alone or together with one or more of the above-described second therapeutic agents in the manufacture of a medicament, either as a single composition or as separate dosage forms, for treatment or prevention in a patient of a disease, disorder or symptom set forth above. Another aspect of the invention is a compound of Formula I for use in the treatment or prevention in a patient of a disease, disorder or symptom thereof delineated herein.

EXEMPLIFICATION

Exemplary Synthesis

The following abbreviations are used in the examples described below
DCM dichloromethane
DMF N,N-dimethylformamide
DMSO dimethyl sulfoxide
EA ethyl acetate
FCC flash column chromatography
h hour(s)
HPLC high-performance liquid chromatography LCMS liquid chromatography-mass spectrometry
mCPBA 3-Chloroperbenzoic acid
MeOH methanol
NMR nuclear magnetic resonance
PE petroleum ether
rt room temperature
THF tetrahydrofuran
TLC thin layer chromatography The compounds of the present invention can be prepared in a number of ways well known to those skilled in the art of organic synthesis. By way of example, compounds of the present invention can be synthesized using the methods described below, together with synthetic methods known in the art of synthetic organic chemistry, or variations thereon as appreciated by those skilled in the art. Compounds of the present invention can be synthesized by following the steps outlined in General Scheme 1 which comprises different sequences of assembling intermediates I-a, I-b, I-c, I-d, and I-e. Starting materials are either commercially available or made by known procedures in the reported literature or as illustrated. For example, reagents and deuterated reagents can either be purchased or readily prepared by known methods to prepare compounds described herein such as the compounds of Formulas I, Ia or Ib with greater than 90%, such as greater that 95% deuterium incorporation at each position designated with a D. Such deuterated reagents include $d_5$-ethanol available from Sigma Aldrich at 99.5 atom % D isotopic purity, acetone-$d_6$ available from Sigma Aldrich at 99.9 atom % D isotopic purity and deuterated lithium aluminum hydride ($LiAlD_4$).

The general way of preparing compounds of Formula (I) using intermediates I-a, I-b, I-c, I-d, and I-e is outlined in General Scheme 1.

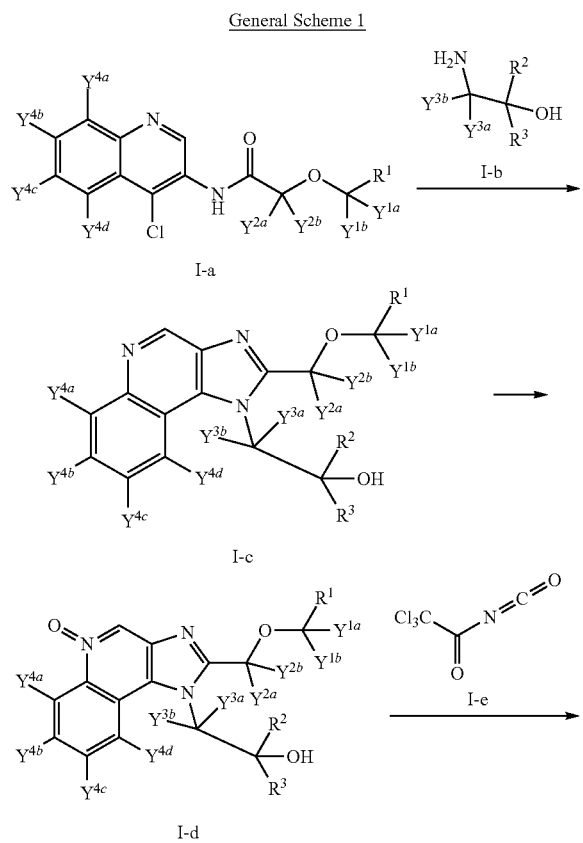

General Scheme 1

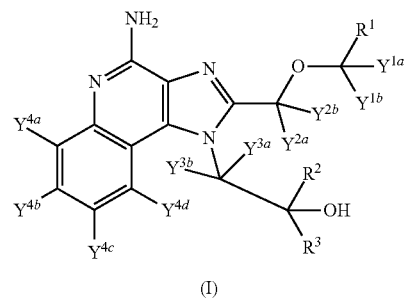

(I)

wherein $Y^{1a}$, $Y^{1b}$, $Y^{2a}$, $Y^{2b}$, $Y^{3a}$, $Y^{3b}$, $Y^{4a}$, $Y^{4b}$, $Y^{4c}$, $Y^{4d}$, $R^1$, $R^2$, and $R^3$ are defined as in Formula (I), above.

In General Scheme 1, cyclization of 1-a and 1-b in the presence of p-toluenesulfonic acid and in a solvent, e.g., ethyl acetate, provides tricyclic intermediate I-c. Oxidation of I-c using an oxidant (e.g., 3-Chloroperbenzoic acid (mCPBA)) in a solvent, e.g., dichloromethane, provides I-d. Treatment of I-d with trichloroacetyl isocyanate in a solvent followed by treatment with a base e.g., sodium methoxide, in a solvent, e.g., methanol, provides the desired compound of Formula (I).

In General Scheme 1, cyclization of 1-a and 1-b in the presence of p-toluenesulfonic acid and in a solvent, e.g., ethyl acetate, provides tricyclic intermediate I-c. Oxidation of I-c using an oxidant (e.g., 3-Chloroperbenzoic acid (mCPBA)) in a solvent, e.g., dichloromethane, provides I-d. Treatment of I-d with trichloroacetyl isocyanate in a solvent followed by treatment with a base e.g., sodium methoxide, in a solvent, e.g., methanol, provides the desired compound of Formula (I).

Example 1: Compound 107, 1-(4-amino-2-((ethoxy-$d_5$)methyl)-1H-imidazo[4,5-c]quinolin-1-yl)-2-methylpropan-2-ol

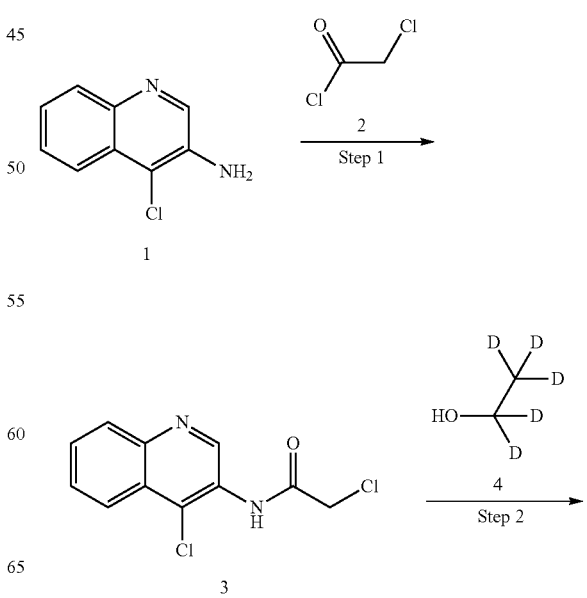

-continued

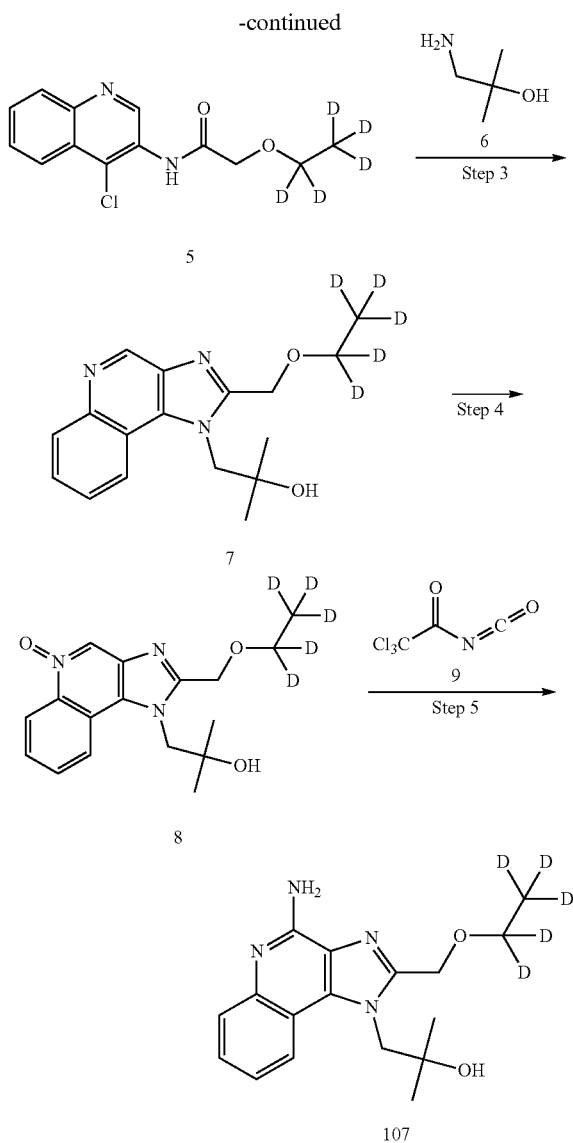

Step 1.
2-chloro-N-(4-chloroquinolin-3-yl)acetamide
(Compound 3)

To a solution of compound 1 (2.0 g, 11.2 mmol, 1 eq) and triethylamine (3.4 g, 33.6 mmol, 3 eq) in DCM (40 mL) at 0° C. was added chloroacetyl chloride (2.52 g, 22.4 mmol, 2 eq) and the resulting mixture was stirred overnight at rt. The reaction mixture was washed with 1N HCl, water and brine, and concentrated in vacuo. The crude residue was purified via FCC (eluting with PE/EA: 1/1) to give compound 3 (1.2 g, 39.5%). TLC: eluting with PE/EA: 1/1; compound 1 Rf=0.4; compound 3 Rf=0.6.

Step 2. N-(4-chloroquinolin-3-yl)-2-(ethoxy-$d_5$)
acetamide (Compound 5)

To a mixture of sodium hydride (0.42 g, 60% in oil, 10.6 mmol, 3.0 eq) in THF at 0° C. was added ethanol-$d_5$ (4, 0.54 g, 10.6 mmol, 3.0 eq) in THF (10 mL) and the resulting mixture was stirred at 0° C. for 0.5 h. tributylammonium iodide (TBAI, 0.27 g) and a solution of compound 3 (0.9 g, 3.52 mmol, 1.0 eq) in THF (10 mL) was then added the resulting mixture was stirred at 60° C. for 12 h. The reaction mixture was quenched with water and extracted with ethyl acetate (3×30 mL). The combined organic layers were washed with water and brine, and dried over $Na_2SO_4$, filtered, concentrated in vacuo. The resulting crude product was purified via FCC (eluting with PE/EA: 1/1) to provide compound 5 (0.5 g, 53%). TLC: eluting with PE/EA: 1/1; compound 3 Rf=0.6; compound 5 Rf=0.5.

Step 3. 1-(2-((ethoxy-$d_5$)methyl)-1H-imidazo[4,5-c]
quinolin-1-yl)-2-methylpropan-2-ol (Compound 7)

A mixture of compound 5 (0.5 g, 1.86 mmol, 1 eq), compound amine 6 (0.25 g, 2.79 mmol, 1.5 eq) and p-toluenesulfonic acid (50 mg, eq) were heated in a sealed tube at 125° C. for 15 h and the reaction mixture was then allowed to cool to rt. Dichloromethane and saturated aqueous $NaHCO_3$ were added, and the resulting mixture was stirred for 15 min. The organic layer was separated and washed sequentially with saturated aqueous $NaHCO_3$ and water, dried over $K_2CO_3$, filtered and concentrated in vacuo. The crude residue was purified via FCC (eluting with DCM/MeOH: 15/1) to provide compound 7 (0.6 g, 94%). TLC: eluting with DCM/MeOH: 10/1; compound 5 Rf=0.9; compound 7 Rf=0.4.

Step 4. 2-((ethoxy-$d_5$)methyl)-1-(2-hydroxy-2-methylpropyl)-1H-imidazo[4,5-c]quinoline 5-oxide
(Compound 8)

To a solution of compound 7 (0.6 g, 1.96 mmol, 1 eq) in dichloromethane (10 mL) at 0° C. was added mCPBA (0.68 g, 3.92 mmol, 2 eq). The resulting mixture was then stirred for 10 min at 0° C., and then at room temperature for 3 h. The reaction was diluted with dichloromethane (20 mL) and saturated aqueous sodium bicarbonate (25 mL), and then stirred for 15 minutes. The aqueous layer was separated and extracted with dichloromethane (3×25 mL), and the combined organic fractions were dried over potassium carbonate, filtered, and concentrated under reduced pressure. The crude residue was purified via FCC (eluting with DCM/MeOH: 15/1) to provide compound 8 (0.5 g, 79%). TLC: eluting with DCM/MeOH: 10/1; compound 7 Rf=0.4; compound 8 Rf=0.3.

Step 5. 1-(4-amino-2-((ethoxy-$d_5$)methyl)-1H-imidazo[4,5-c]quinolin-1-yl)-2-methylpropan-2-ol
(Compound 107)

Figure 1B:
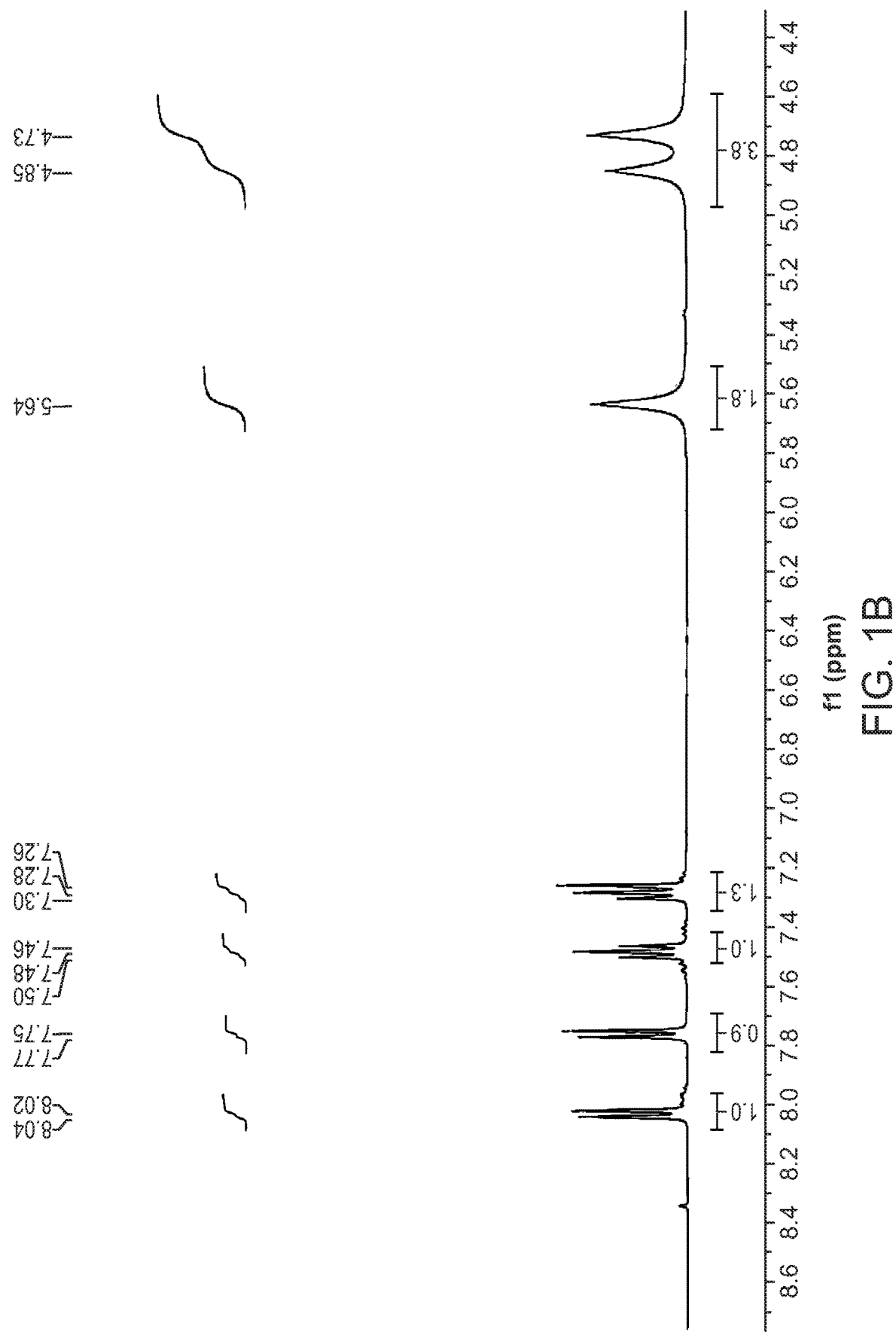
Figure 1C:
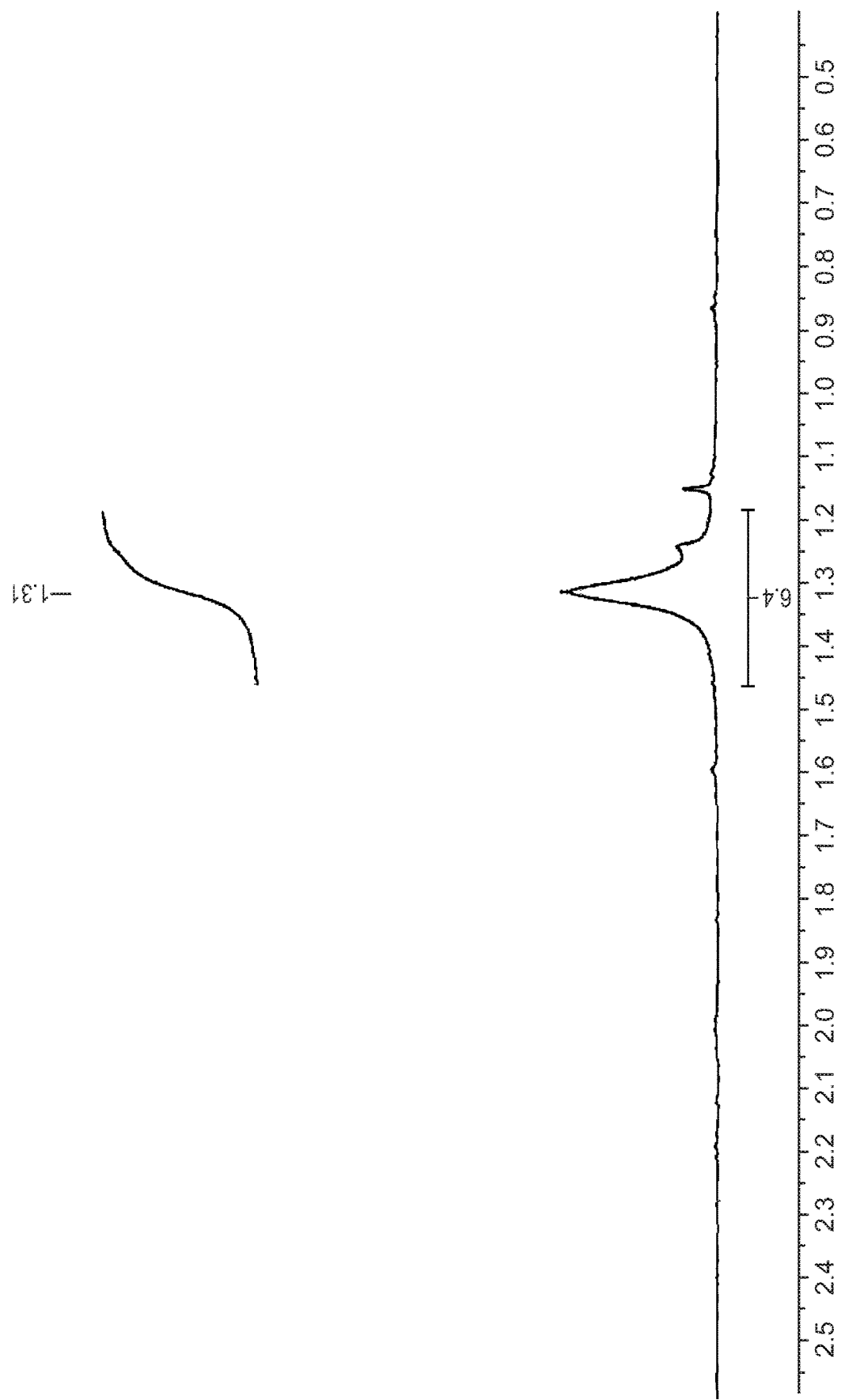

To a solution of compound 8 (0.3 g, 0.94 mmol, 1 eq) in dichloromethane (10 mL) at 0° C. was added trichloroacetyl isocyanate 9 (0.29 g, 1.55 mmol, 1.66 eq) with stirring. The reaction was stirred at 0° C. for 15 minutes, and then at 55° C. for 1 h. The mixture was concentrated under reduced pressure and the resulting residue was dissolved in methanol (10 mL). Sodium methoxide (0.46 g, 8.43 mmol, 9.0 eq) was added and the resulting mixture was stirred at 55° C. for 2 h and then cooled to room temperature. The mixture was concentrated under reduced pressure and the resulting residue was purified by FCC (eluting with DCM/MeOH: 15/1) to provide compound I-1 (0.15 g, 50%). TLC: eluting with DCM/MeOH: 10/1; compound 8 Rf=0.3; compound 107 Rf=0.4. $^1$H NMR in $CDCl_3$ is shown in FIGS. 1A through 1C. LCMS: m/z 320.25 [M+H]$^+$.

27

Example 2: Compound 104, 2-((4-amino-2-(ethoxymethyl)-1H-imidazo[4,5-c]quinolin-1-yl)methyl)propan-1,1,1,3,3,3-$d_6$-2-ol

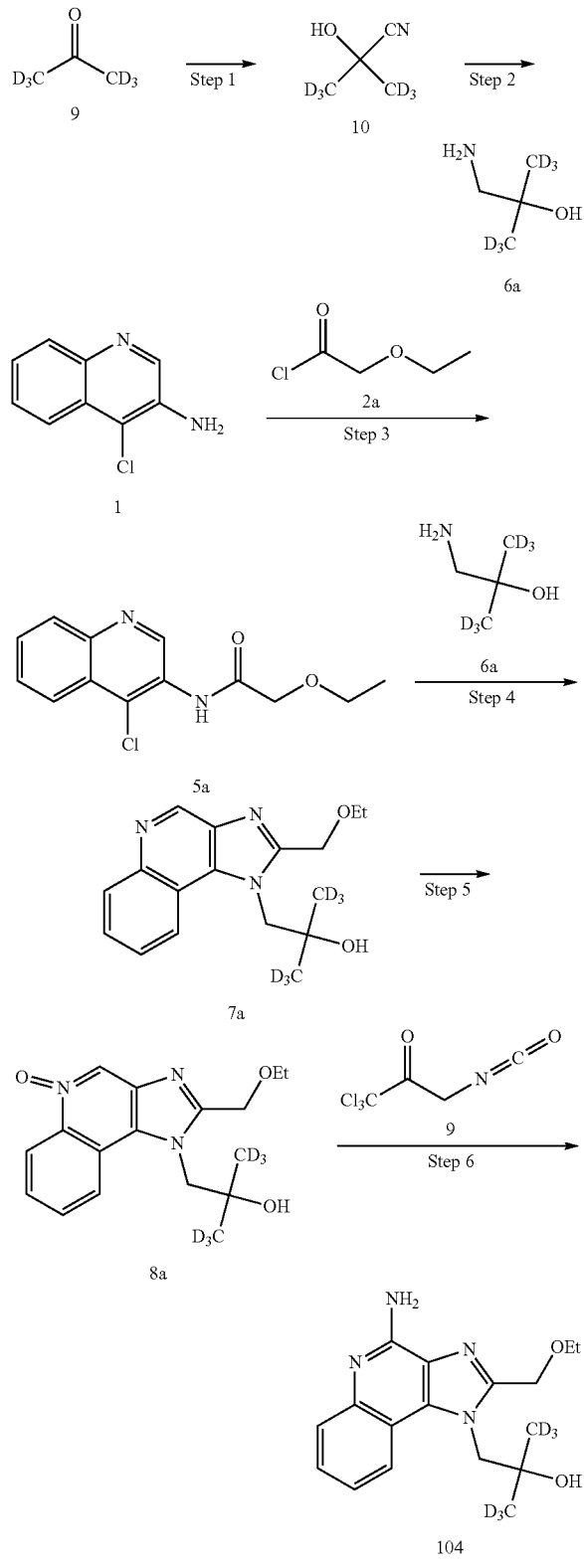

28

Step 1. 2-hydroxy-2-(methyl-$d_3$)propanenitrile-3,3,3-$d_3$ (10)

To a solution of acetone-$d_6$ (10 g, 249 mmol, 1 eq) in DCM (100 mL) was added TMS-CN (29.7 g, 299 mmol, 1.2 eq) and zinc chloride (7.9 g, 24.9 mmol, 0.1 eq) at 0° C. and the resulting mixture was stirred at rt overnight. The reaction was quenched with water and extracted with ethyl acetate (3×30 mL). The combined organic layers were dried over Na$_2$SO$_4$, filtered, concentrated in vacuo to provide crude compound 10 (9.1 g 55%) which was used in the next step without further purification.

Step 2. 2-(Aminomethyl)propan-1,1,1,3,3,3-$d_6$-2-ol (6a)

To a solution of compound 10 (3.0 g, 44.7 mmol, 1 eq) in THF (30 mL) at 0° C. was added LiAlH$_4$ (3.4 g, 89.4 mmol, 2 eq) and the resulting mixture was stirred at 70° C. for 3 h. The reaction mixture was quenched with water and extracted with ethyl acetate (3×100 mL). The combined organic layers were dried over sodium sulfate, filtered, and concentrated to provide crude compound 6a (0.9 g, 28%), which was used for next step without further purification.

Step 3. N-(4-chloroquinolin-3-yl)-2-ethoxyacetamide (5a)

Compound 1 (1.0 g, 5.6 mmol, 1 eq) and triethylamine (1.7 g, 16.8 mmol, 3 eq) were dissolved in DCM (20 mL) and the resulting mixture was cooled to 0° C. Compound 2a (1.37 g, 11.2 mmol, 2 eq) was added and the resulting mixture was stirred at rt overnight. The mixture was washed with 1 N HCl, concentrated in vacuo. The resulting crude product was purified via FCC (eluting with PE/EA: 1/1) to afford compound 5a (0.6 g, 40%). TLC: eluting with PE/EA: 1/1; compound 1 Rf=0.4; compound 5a Rf=0.5.

Step 4. 2-((2-(ethoxymethyl)-1H-imidazo[4,5-c]quinolin-1-yl)methyl)propan-1,1,1,3,3,3-$d_6$-2-ol (7a)

A mixture of compound 5a (0.5 g, 1.78 mmol, 1 eq), compound 6a (0.25 g, 3.5 mmol, 2 eq) and p-toluenesulfonic acid (0.05 g) in a TEFLON-lined pressure vessel was heated at 125° C. for 15 h and them allowed to cool to rt. Dichloromethane (50 mL) and saturated aqueous NaHCO$_3$ (10 mL) were added, and the resulting mixture was stirred for 15 min. The organic layer was separated and washed sequentially with saturated aqueous NaHCO$_3$ and water, dried over K$_2$CO$_3$, filtered and concentrated in vacuo. The product was purified via FCC (eluting with DCM/MeOH: 15/1) to provide compound 7a (0.6 g, 99%). TLC: eluting with DCM/MeOH: 10/1; compound 5a Rf=0.9; compound 7a Rf=0.4.

Step 5. 2-(ethoxymethyl)-1-(2-hydroxy-2-(methyl-$d_3$)propyl-3,3,3-$d_3$)-1H-imidazo[4,5-c]quinoline 5-oxide (8a)

To a solution of compound 7a (0.4 g, 1.42 mmol, 1 eq) in dichloromethane (10 mL) at 0° C. was added mCPBA (0.49 g, 2.84 mmol, 2 eq). The resulting mixture was stirred at 0° C. for ten minutes and then at room temperature for 3 h hours. The reaction mixture was diluted with dichloromethane (20 mL) and saturated aqueous sodium bicarbonate (25 mL), and then stirred for 15 minutes. The aqueous layer was separated and extracted with dichloromethane (3×25 mL).

The combined organic fractions were dried over potassium carbonate, filtered, and concentrated under reduced pressure. The crude product was purified via FCC (eluting with DCM/MeOH: 15/1) to provide compound 8a (0.2 g, 47%). TLC: eluting with DCM/MeOH: 10/1; compound 7a Rf=0.4; compound 8a Rf=0.3.

Step 6. 2-((4-amino-2-(ethoxymethyl)-1H-imidazo[4,5-c]quinolin-1-yl)methyl)propan-1,1,1,3,3,3-$d_6$-2-ol (104)

Figure 2A:
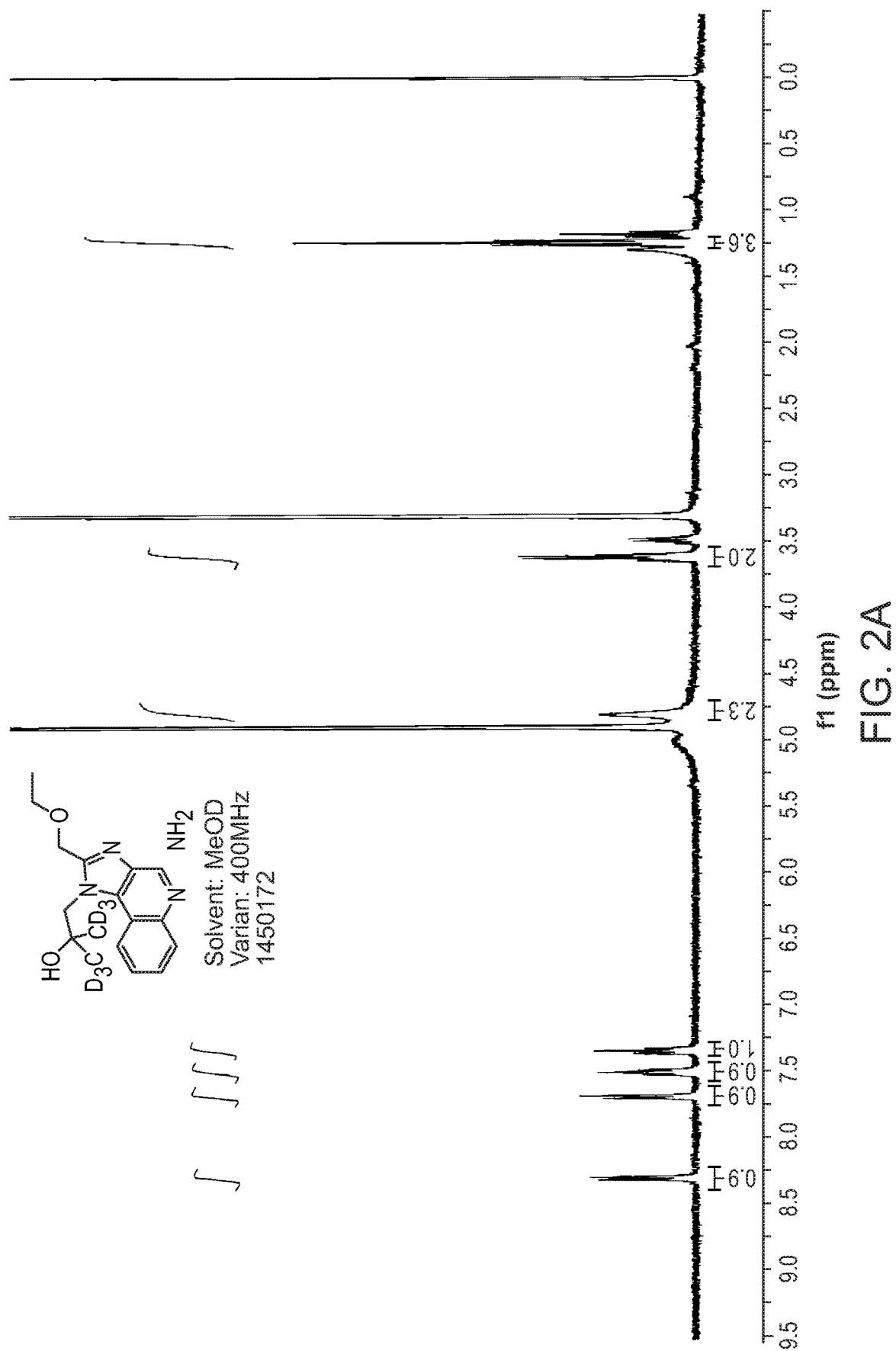
FIGS. 2A-2C, in combination, represent an $^1$H NMR spectrum of compound 104 plotted as signal intensity (vertical axis) vs. chemical shift (in ppm on the horizontal axis). Signal integration also shown.
Figure 2B:
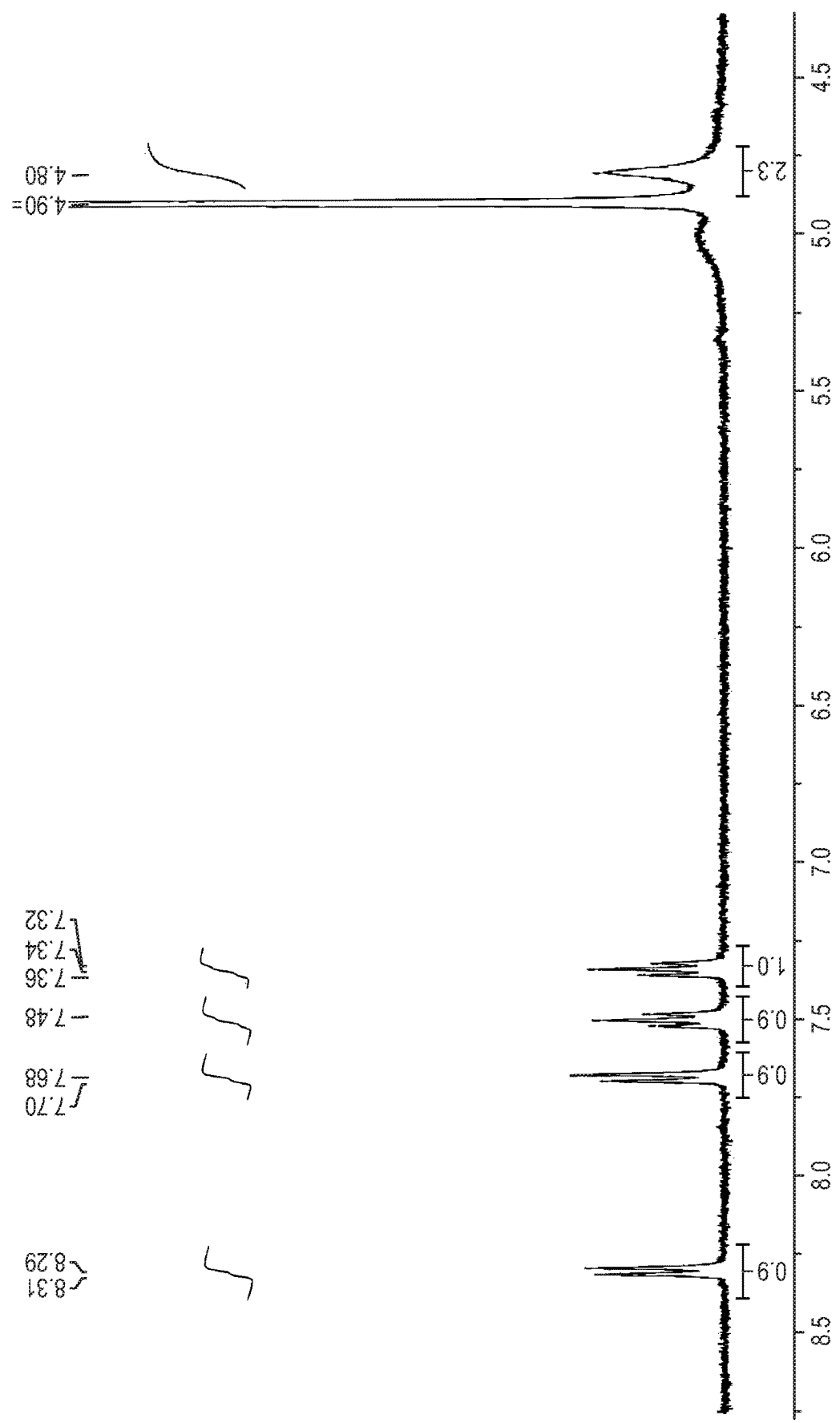
Figure 2C:
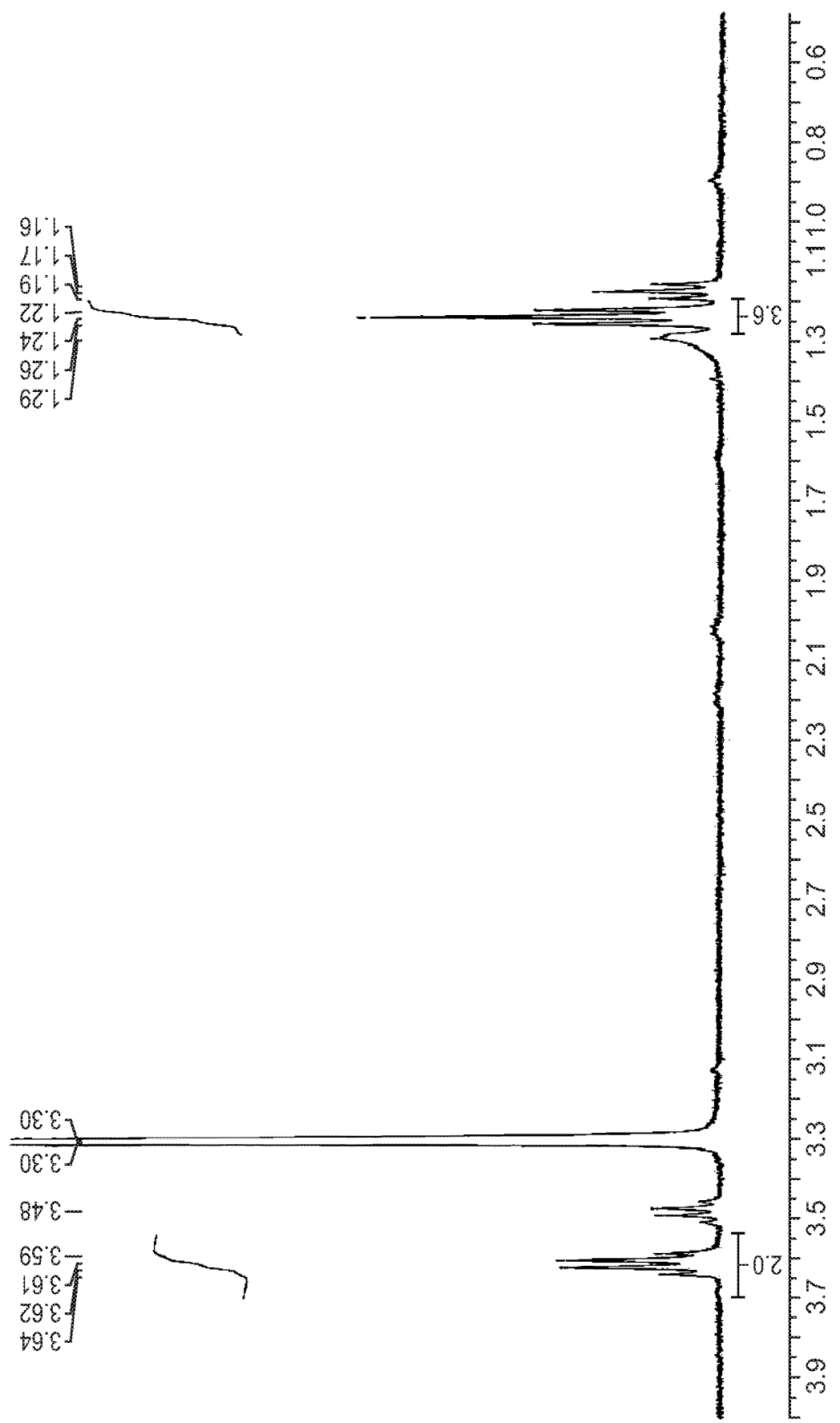

To a solution of compound 8a (0.25 g, 0.84 mmol, 1 eq) in dichloromethane (10 mL) at 0° C. was added trichloroacetyl isocyanate 9 (0.26 g, 1.4 mmol, 1.66 eq) with stirring. The reaction was stirred at 0° C. for 15 minutes and then at 55° C. for 1 h. The reaction mixture was concentrated under reduced pressure and the resulting residue was dissolved in methanol (10 mL). Sodium methoxide (0.41 g, 7.56 mmol, 9 eq) was added and the resulting mixture was stirred at 55° C. for 2 h, cooled to room temperature, and concentrated under reduced pressure. The crude residue was purified via FCC (eluting with DCM/MeOH: 15/1) to provide 104 (110 mg, 44%). TLC: eluting with DCM/MeOH: 10/1; compound 8a Rf=0.4; I-2 Rf=0.4. $^1$H NMR in MeOD is shown in FIGS. 2A through 2C. LCMS: m/z 321.3 [M+H]$^+$.

Example 3: Compound 113, 1-(4-amino-2-(ethoxymethyl)-1H-imidazo[4,5-c]quinolin-1-yl)-2-(methyl-$d_3$)propan-1,1,3,3,3-$d_5$-2-ol

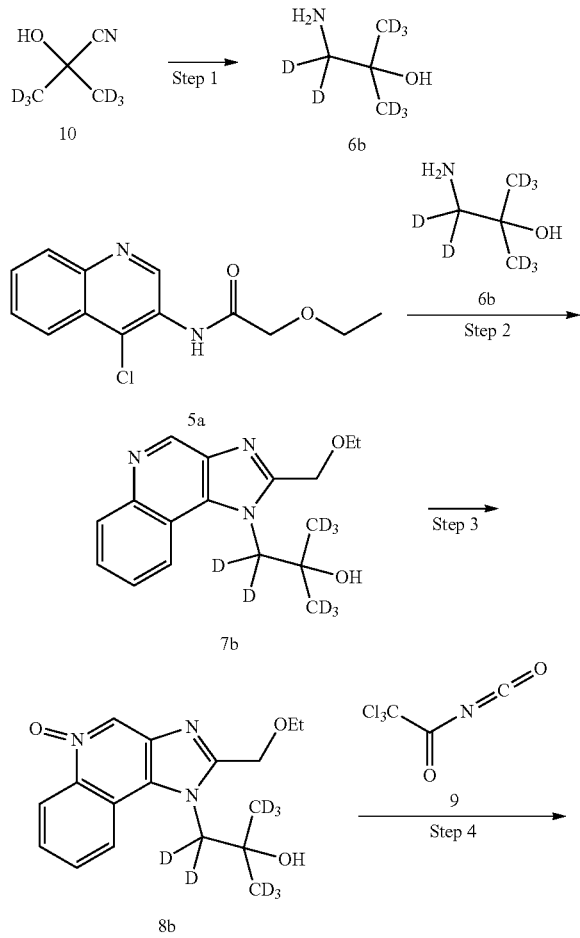

-continued

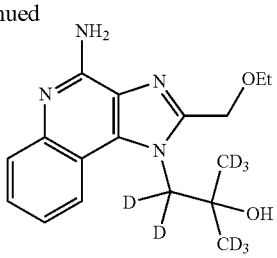

113

Step 1. 1-amino-2-(methyl-$d_3$)propan-1,1,3,3,3-$d_5$-2-ol (6b)

To a solution of compound 10 (3.0 g, 44.7 mmol, 1 eq) in THF (30 mL) was added LiAlD$_4$ (3.4 g, 89.4 mmol, 2 eq) at 0° C. The mixture was stirred at 70° C. for 3 h. The reaction was quenched with water and extracted with ethyl acetate (3×30 mL). The organic layers were dried with Na$_2$SO$_4$, filtered and concentrated to provide compound 6b (1.0 g, 30%).

Step 2. 1-(2-(ethoxymethyl)-1H-imidazo[4,5-c]quinolin-1-yl)-2-(methyl-$d_3$)propan-1,1,3,3,3-$d_5$-2-ol (7b)

A mixture of compound 5a (0.5 g, 1.78 mmol, 1 eq), compound 6b (0.26 g, 3.56 mmol, 2 eq) and p-toluenesulfonic acid (50 mg) was heated in a sealed vessel at 125° C. for 15 h and allowed to cool to rt. Dichloromethane and saturated aqueous NaHCO$_3$ were added, and the mixture was stirred for 15 min. The organic layer was separated and washed sequentially with saturated aqueous NaHCO$_3$ and water, dried over K$_2$CO$_3$, filtered, and concentrated in vacuo. The crude residue was purified via FCC (eluting with DCM/MeOH: 15/1) to provide compound 7b (0.5 g, 93%). TLC: eluting with DCM/MeOH: 10/1; compound 5a Rf=0.9; compound 7b Rf=0.4.

Step 3. 2-(ethoxymethyl)-1-(2-hydroxy-2-(methyl-$d_3$)propyl-1,1,3,3,3-$d_5$)-1H-imidazo[4,5-c]quinoline 5-oxide (8b)

To a solution of compound 7b (0.5 g, 1.76 mmol, 1 eq) in dichloromethane (10 mL) at 0° C. was added mCPBA (0.43 g, 2.52 mmol, 2 eq). The reaction was stirred at room temperature for three hours, diluted with dichloromethane (20 mL), and saturated aqueous sodium bicarbonate (25 mL), and stirred for 15 minutes. The aqueous layer was separated and extracted with dichloromethane (3×25 mL). The combined organic layers were dried over potassium carbonate, filtered, and concentrated under reduced pressure. The crude residue was purified via FCC (eluting with DCM/MeOH: 15/1) to provide compound 8b (0.18 g, 34%). TLC: eluting with DCM/MeOH: 10/1; compound 7b Rf=0.4; compound 8b Rf=0.3.

Step 4. 1-(4-amino-2-(ethoxymethyl)-1H-imidazo[4,5-c]quinolin-1-yl)-2-(methyl-$d_3$)propan-1,1,3,3,3-$d_5$-2-ol (113)

Figure 3A:
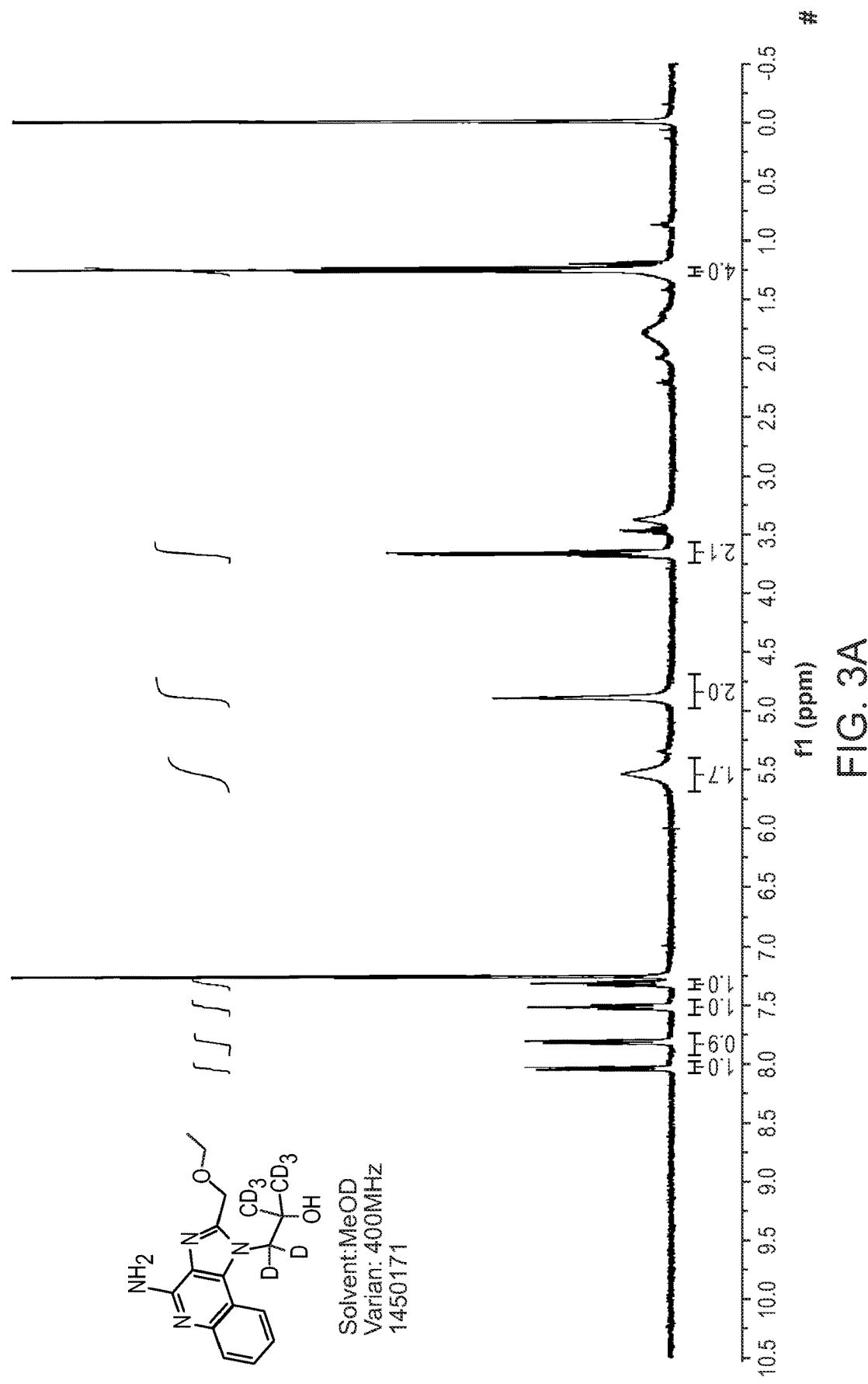
FIGS. 3A-3C, in combination, represent an $^1$H NMR spectrum of compound 113 plotted as signal intensity (vertical axis) vs. chemical shift (in ppm on the horizontal axis). Signal integration also shown.
Figure 3B:
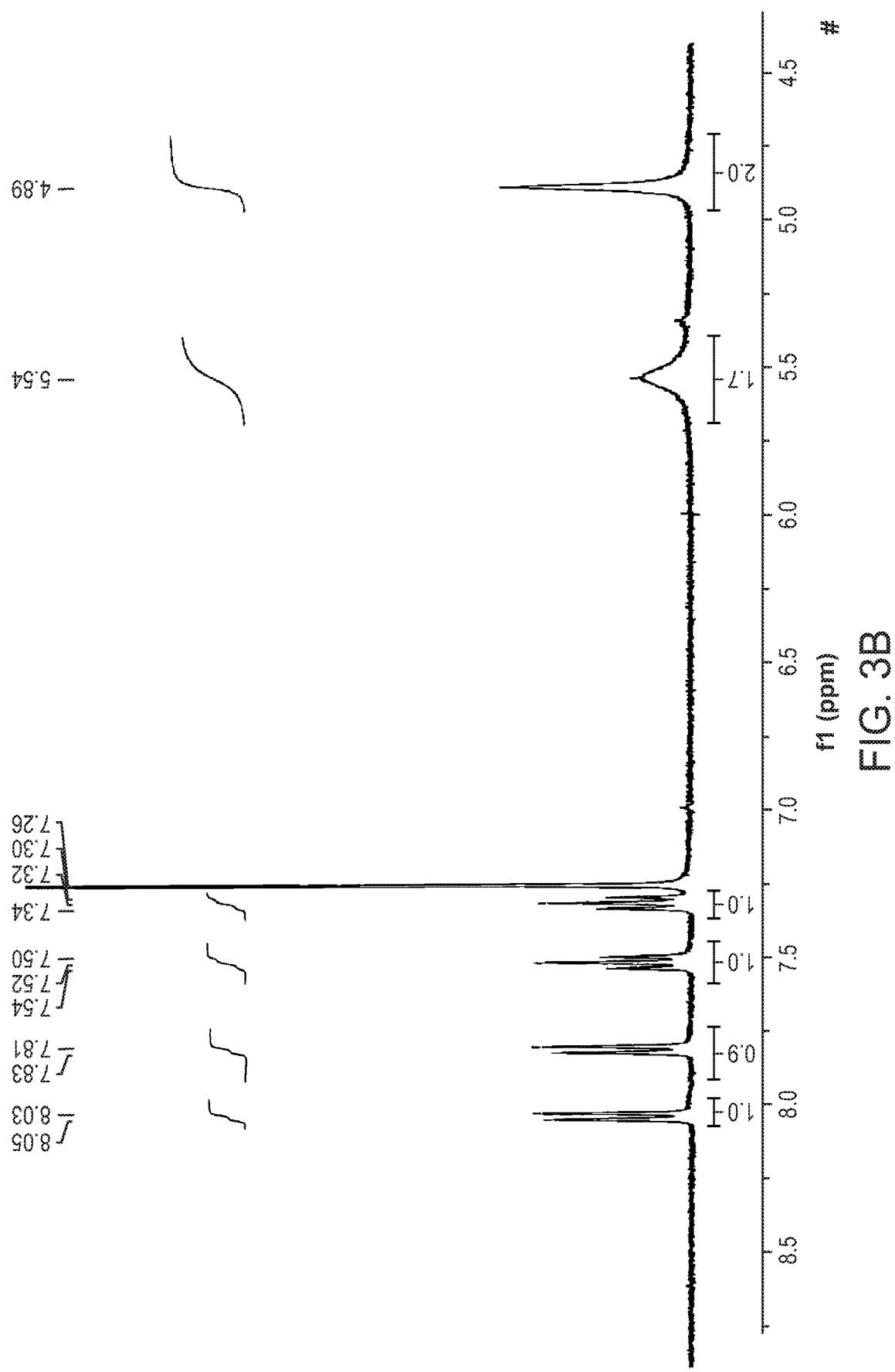
Figure 3C:
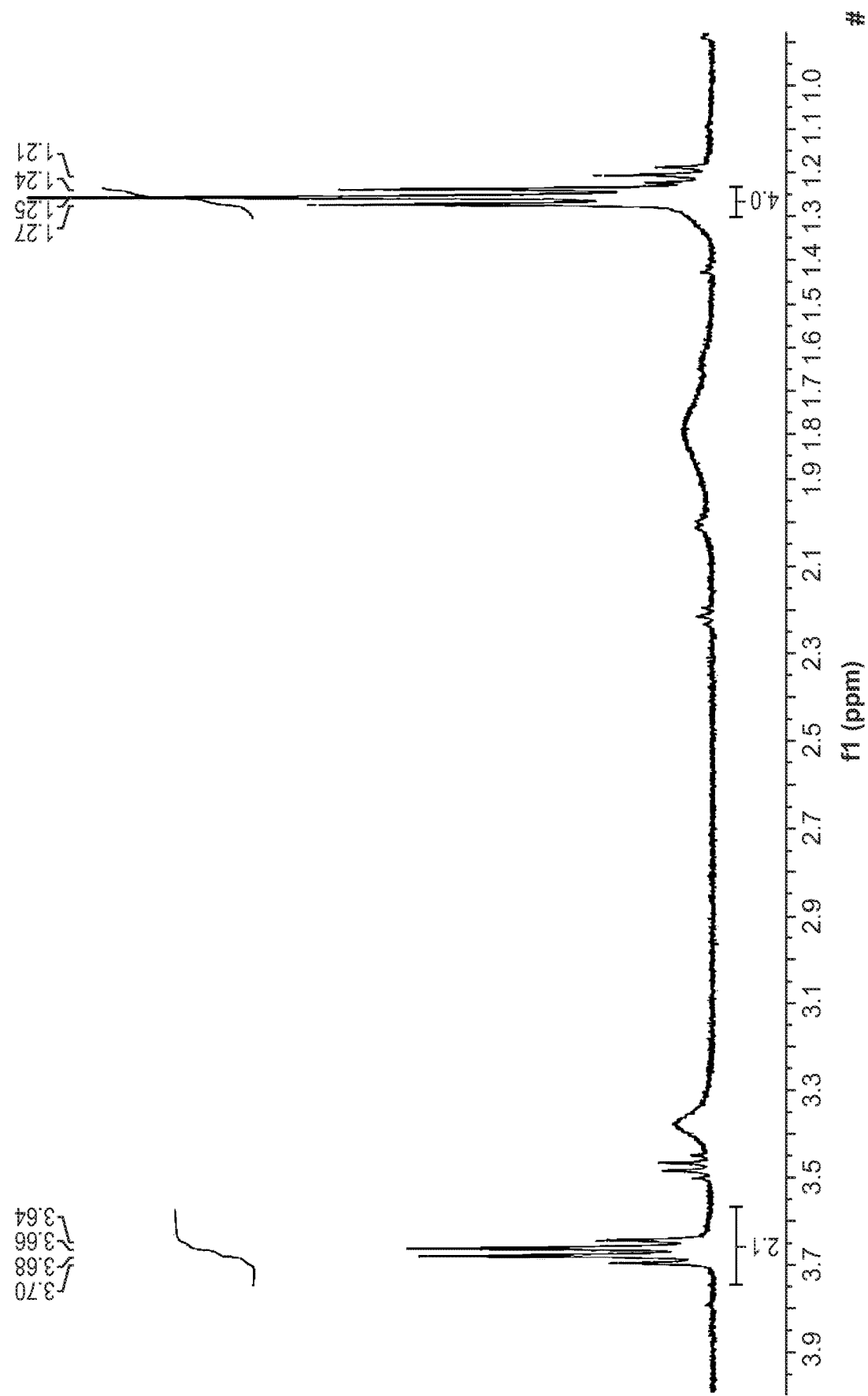

To a solution of compound 8b (0.18 g, 0.6 mmol, 1 eq) in dichloromethane (10 mL) at 0° C. was added trichloroacetyl isocyanate (0.19 g, 1.0 mmol, 1.66 eq) with stirring. The reaction mixture was heated at 55° C. for 1 h and then concentrated under reduced pressure. The resulting residue was dissolved in methanol (10 mL), and sodium methoxide (0.29 g, 5.4 mmol, 9 eq) was added. The mixture was stirred at 55° C. for 2 h, and then allowed to cool to room temperature and concentrated under reduced pressure. The crude residue was purified via FCC (eluting with DCM/MeOH: 15/1) to provide 113 (0.12 g, 67%). TLC: eluting with DCM/MeOH: 10/1; compound 8b Rf=0.4. $^1$H NMR in MeOD is shown in FIG. 3. LCMS: m/z 323.3 [M+H]$^+$.

Example 4: Preparation of Compound 116

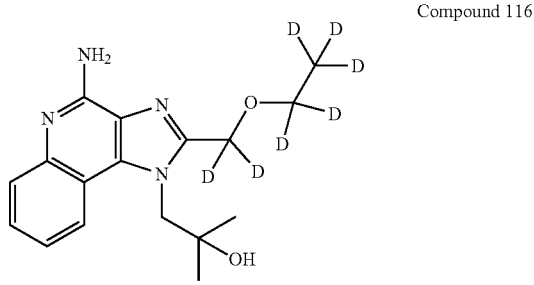 [SMILES: [2H]C([2H])(OC([2H])([2H])C([2H])([2H])[2H])c1nc2c(N)nc3ccccc3c2n1CC(C)(C)O]

Compound 116

Compound 116 is prepared according to the synthetic procedure used in Example 1 except that the chloroacetyl chloride used in Step 1 of Example 1 was substituted with 2-chloroacetyl chloride-d$_2$.

Example 5: Preparation of Compound 101

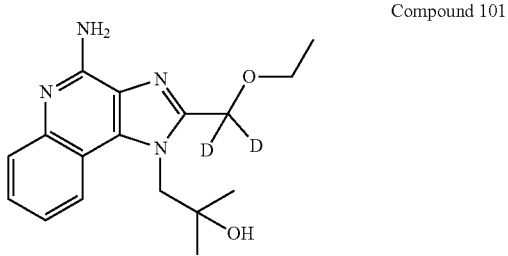 [SMILES: [2H]C([2H])(OCC)c1nc2c(N)nc3ccccc3c2n1CC(C)(C)O]

Compound 101

Compound 101 is prepared according to the synthetic procedure used in Example 1 except that the chloroacetyl chloride used in Step 1 of Example 1 was substituted with 2-chloroacetyl chloride-d$_2$ and that the ethanol-d$_5$ used in Step 2 of Example 1 was substituted with ethanol.

Example 6: Preparation of Compound 105

Compound 105 is prepared according to the synthetic procedure used in Example 1 except that the chloroacetyl chloride used in Step 1 of Example 1 was substituted with 2-chloroacetyl chloride-d$_2$ and that the ethanol-d$_5$ used in Step 2 of Example 1 was substituted with ethanol-d$_2$ (CH$_3$CD$_2$OH).

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (i.e., R$^1$, R$^2$, R$^3$, etc.) or not. The suitability of a chemical group in a compound structure for use in the synthesis of another compound is within the knowledge of one of ordinary skill in the art.

Additional methods of synthesizing compounds of Formula I and their synthetic precursors, including those within routes not explicitly shown in schemes herein, are within the means of chemists of ordinary skill in the art. Synthetic chemistry transformations and protecting group methodologies (protection and deprotection) useful in synthesizing the applicable compounds are known in the art and include, for example, those described in Larock R, *Comprehensive Organic Transformations*, VCH Publishers (1989); Greene T W et al., *Protective Groups in Organic Synthesis*, 3$^{rd}$ Ed., John Wiley and Sons (1999); Fieser L et al., *Fieser and Fieser's Reagents for Organic Synthesis*, John Wiley and Sons (1994); and Paquette L, ed., *Encyclopedia of Reagents for Organic Synthesis*, John Wiley and Sons (1995) and subsequent editions thereof.

Combinations of substituents and variables envisioned by this invention are only those that result in the formation of stable compounds.

Example 7: Pharmacokinetic Analysis

Figure 4:
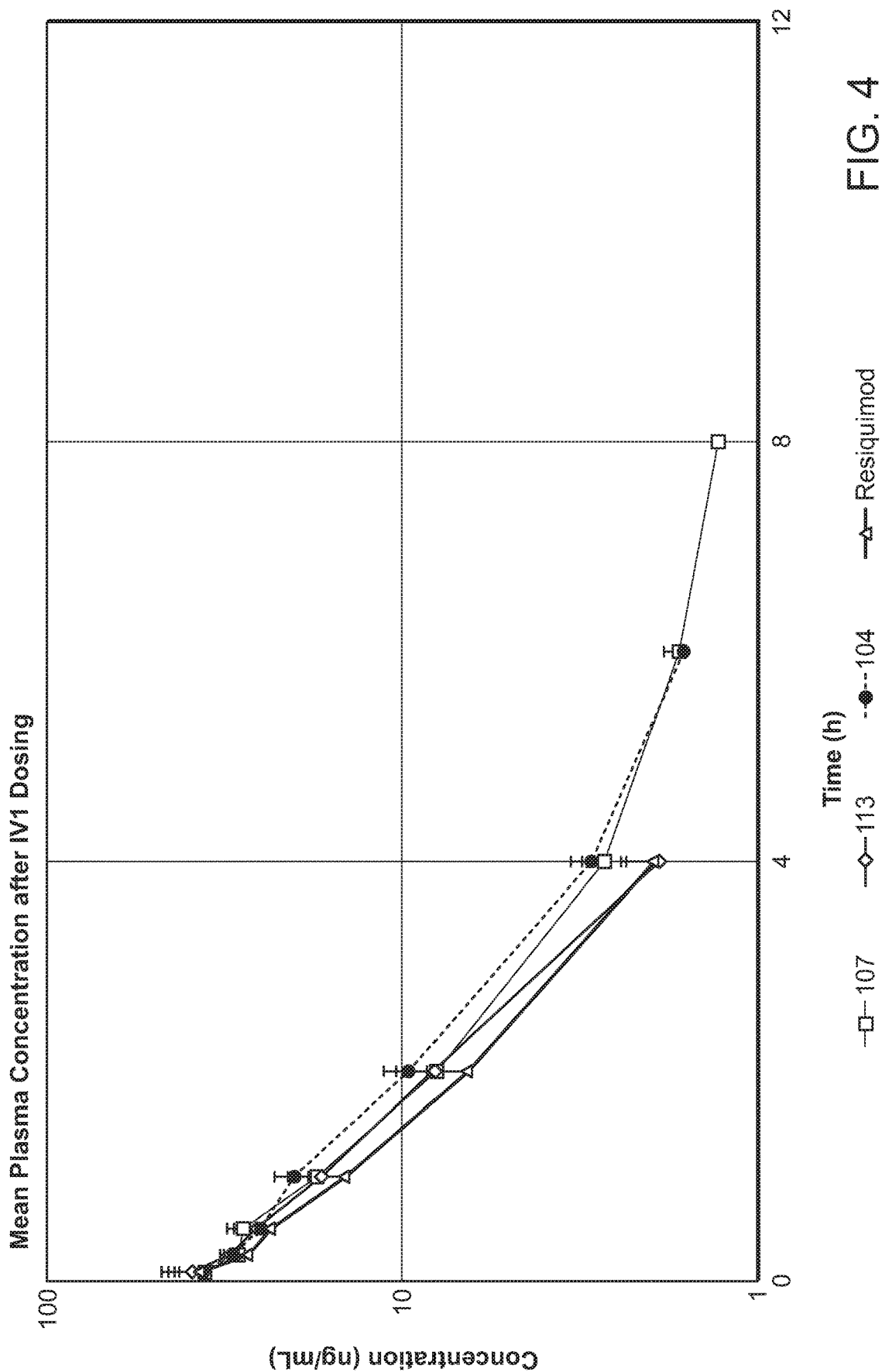
FIG. 4 is a graph of mean plasma concentration versus time for rats administered the indicated compound.

Compounds 107, 113 and 104 and resiquimod (non-deuterated) were administered to male SD rats and pharmacokinetic analysis performed. Each of the tested compounds was administered as an IV bolus (3 rats per group) at a dose 0.04 mg/kg. Rats were fasted at least 12 hours prior to administration of test compound. All rats had access to Certified Rodent Chow ad libitum four hours post dosing Blood samples were collected at the following time points post-dosing: 5 mins., 15 mins., 30 mins., 1 hr., 2 hrs., 4 hrs. 6 hrs., 8 hrs., 12 hrs. and 24 hrs. Blood samples were processed for plasma and analyzed by LC-MS/MS for the following pharmacokinetic parameters: $C_{max}$, $T_{1/2}$, CL, $V_{dss}$, AUC$_{0-last}$, AUC$_{0-\infty}$, MRT$_{0-last}$, and MRT$_{0-\infty}$. Comparison of $T_{1/2}$, is set forth in Table 1 and a graph of plasma concentration versus time is set forth in FIG. 4.

| Test Compound | $T_{1/2}$, ± SD (hours) | $C_{max}$ (ng/mL) |
|---|---|---|
| Resiquimod | 1.03 ± 1.72 | 43.8 ± 10.9 |
| Compound 107 | 2.41 ± 1.71 | 40.1 ± 8.82 |
| Compound 113 | 1.97 ± 1.76 | 44.5 ± 14.2 |
| Compound 104 | 1.85 ± 1.05 | 40.3 ± 10.7 |

Other pharmacokinetic parameters measured included: CL (Apparent total body clearance of the drug from plasma (mL/min/kg)); Vd$_{ss}$ (Apparent volume of distribution at equilibrium determined after intravenous administration ((L/kg)); AUC$_{0-last}$ (Area under the plasma concentration-time curve from time zero to time of last measurable concentration (ng·hr/mL)); AUC$_{0-inf}$ (Area under the concentration-time curve from zero up to $\infty$ (ng·hr/mL)); MRT$_{0-last}$ (Mean Residence Time of the drug (hours)); and MRT$_{0-inf}$ (Mean Residence Time of the drug (hours)) and data is set forth below.

| Test Compound | CL (mL/min/kg) | $V_{dss}$ (L/kg) | $AUC_{0-last}$ (ng·hr/mL) | $AUC_{0-inf}$ (ng·hr/mL) | $MRT_{0-last}$ (hours) | $MRT_{0-Inf}$ (hours) |
|---|---|---|---|---|---|---|
| Resiquimod | 30.1 ± 4.66 | 2.46 ± 0.361 | 42.1 ± 6.04 | 45.9 ± 6.67 | 1.09 ± 0.0810 | 1.37 ± 0.139 |
| Cmpd. 107 | 22.7 ± 3.27 | 3.23 ± 0.581 | 54.8 ± 6.02 | 59.4 ± 8.16 | 1.66 ± 0.151 | 2.43 ± 0.735 |
| Cmpd. 113 | 25.9 ± 5.35 | 2.61 ± 0.732 | 49.3 ± 8.99 | 53.0 ± 11.2 | 1.26 ±-.345 | 1.79 ± 0.884 |
| Cmpd. 104 | 22.3 ± 2.74 | 2.62 ± 0.516 | 56.2 ± 6.51 | 60.4 ± 7.71 | 1.50 ± 0.328 | 2.10 ± 0.663 |

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention. All the patents, journal articles and other documents discussed or cited above are herein incorporated by reference.

What is claimed is:

1. A compound having structural formula I:

or a pharmaceutically acceptable salt thereof, wherein:
each of $R^1$, $R^2$ and $R^3$ is independently selected from —$CH_3$, and —$CD_3$; and
each of $Y^{1a}$, $Y^{1b}$, $Y^{2a}$, $Y^{2b}$, $Y^{3a}$, $Y^{3b}$, $Y^{4a}$, $Y^{4b}$, $Y^{4c}$, and $Y^{4d}$ is independently selected from hydrogen and deuterium;
wherein each position that is designated as containing deuterium has at least 50.1% deuterium incorporation at that position and at least $R^1$ or both $R^2$ and $R^3$ are $CD_3$.

2. The compound of claim 1, wherein:
$Y^{1a}$ and $Y^{1b}$ are the same;
$Y^{2a}$ and $Y^{2b}$ are the same;
$Y^{3a}$ and $Y^{3b}$ are the same; and
$Y^{4a}$, $Y^{4b}$, $Y^{4c}$, and $Y^{4d}$ are the same.

3. The compound of claim 1, wherein each of $Y^{4a}$, $Y^{4b}$, $Y^{4c}$, and $Y^{4d}$ is hydrogen.

4. The compound of claim 1, wherein each of $Y^{1a}$ and $Y^{1b}$ is deuterium, each of $Y^{1a}$ and $Y^{1b}$ is hydrogen, each of $Y^{2a}$ and $Y^{2b}$ is deuterium, each of $Y^{2a}$ and $Y^{2b}$ is hydrogen, each of $Y^{3a}$ and $Y^{3b}$ is deuterium, or each of $Y^{3a}$ and $Y^{3b}$ is hydrogen.

5. The compound of claim 1, wherein $R^1$ is —$CD_3$.

6. The compound of claim 1, wherein each of $R^2$ and $R^3$ is —$CD_3$, or each of $R^2$ and $R^3$ is —$CH_3$.

7. The compound of claim 1, wherein each of $Y^{4a}$, $Y^{4b}$, $Y^{4c}$, and $Y^{4d}$ is deuterium, $Y^{1a}$ and $Y^{1b}$ are the same; $Y^{2a}$ and $Y^{2b}$ are the same; $Y^{3a}$ and $Y^{3b}$ are the same; and $R^2$ and $R^3$ are the same.

8. The compound of claim 7, wherein the compound is selected from:

or a pharmaceutically acceptable salt thereof.

9. The compound of claim 1, wherein each of $Y^{4a}$, $Y^{4b}$, $Y^{4c}$, and $Y^{4d}$ is hydrogen; $Y^{1a}$ and $Y^{1b}$ are the same; $Y^{2a}$ and $Y^{2b}$ are the same; $Y^{3a}$ and $Y^{3b}$ are the same; and $R^2$ and $R^3$ are the same, the compound selected from any compound in the table below:

| Compound | $Y^{1a}/Y^{1b}$ | $Y^{2a}/Y^{2b}$ | $Y^{3a}/Y^{3b}$ | R1 | $R^2/R^3$ |
|---|---|---|---|---|---|
| 103 | H | H | H | $CD_3$ | $CH_3$ |
| 104 | H | H | H | $CH_3$ | $CD_3$ |
| 107 | D | H | H | $CD_3$ | $CH_3$ |
| 108 | D | H | H | $CH_3$ | $CD_3$ |
| 110 | H | D | H | $CD_3$ | $CH_3$ |
| 111 | H | D | H | $CH_3$ | $CD_3$ |
| 112 | H | H | D | $CD_3$ | $CH_3$ |
| 113 | H | H | D | $CH_3$ | $CD_3$ |
| 114 | H | H | H | $CD_3$ | $CD_3$ |
| 116 | D | D | H | $CD_3$ | $CH_3$ |
| 117 | D | D | H | $CH_3$ | $CD_3$ |
| 118 | D | H | D | $CD_3$ | $CH_3$ |
| 119 | D | H | D | $CH_3$ | $CD_3$ |
| 120 | D | H | H | $CD_3$ | $CD_3$ |
| 121 | H | D | D | $CD_3$ | $CH_3$ |
| 122 | H | D | D | $CH_3$ | $CD_3$ |
| 123 | H | D | H | $CD_3$ | $CD_3$ |
| 124 | H | H | D | $CD_3$ | $CD_3$ |
| 125 | D | D | D | $CD_3$ | $CH_3$ |
| 126 | D | D | D | $CH_3$ | $CD_3$ |
| 127 | D | D | H | $CD_3$ | $CD_3$ |
| 128 | D | H | D | $CD_3$ | $CD_3$ |
| 129 | H | D | D | $CD_3$ | $CD_3$ |
| 130 | D | D | D | $CD_3$ | $CD_3$ | wherein any atom not designated as deuterium or D is present at its natural isotopic abundance.

10. The compound of claim 9, wherein the compound is selected from:

(Compound 107)

(Compound 104)

(Compound 113)

(Compound 116)

or a pharmaceutically acceptable salt thereof.

11. The compound of claim 1, having structural formula Ia:

or a pharmaceutically acceptable salt thereof, wherein:
$R^1$ is selected from —$CH_3$, and —$CD_3$;
$Y^{1a}$ and $Y^{1b}$ are the same; and
$Y^{2a}$ and $Y^{2b}$ are the same.

12. The compound of claim 11, wherein $Y^{2a}$ and $Y^{2b}$ are hydrogen.

13. The compound of claim 11, wherein $R^1$ is —$CD_3$ and each of $Y^{1a}$ and $Y^{1b}$ is deuterium, or $R^1$ is —$CH_3$ and each of $Y^{1a}$ and $Y^{1b}$ is hydrogen.

14. The compound of claim 11, having the following structural formula:

or a pharmaceutically acceptable salt thereof.

15. The compound of claim 1, having structural formula Ib:

or a pharmaceutically acceptable salt thereof, wherein:
each of $R^2$ and $R^3$ is independently selected from —$CH_3$ and —$CD_3$;
$Y^{2a}$ and $Y^{2b}$ are the same; and
$Y^{3a}$ and $Y^{3b}$ are the same.

16. The compound of claim 15, wherein $Y^{2a}$ and $Y^{2b}$ are hydrogen, or $Y^{3a}$ and $Y^{3b}$ are hydrogen.

17. The compound of claim 15, wherein $R^2$ and $R^3$ are the same.

18. The compound of claim 15 having the following structural formula or a pharmaceutically acceptable salt thereof.

19. The compound of claim 1, wherein any atom not designated as deuterium or D is present at its natural isotopic abundance.

20. The compound of claim 1, wherein each position designated as D has greater than 90% deuterium incorporation.

21. A pharmaceutical composition comprising a compound of claim 1; and a pharmaceutically acceptable carrier.

22. A method of treating cutaneous T-cell lymphoma comprising the step of administering to a subject in need thereof a compound of claim 1 or a pharmaceutically acceptable salt thereof.

23. A method of enhancing an immune response to an antigen in a subject comprising the step of co-administering to the subject the antigen and a compound of claim 1 or a pharmaceutically acceptable salt thereof.

24. The method of claim 23, wherein the antigen is selected from a cancer antigen, an influenza antigen and a Hepatitis B virus antigen.

25. The method of claim 23, wherein the cancer antigen is selected from NY-ESO-1 protein, NY-ESO-1b peptide, gp100, MAGE-3, CDX-1401, LPV7, and an autologous tumor lysate.

26. A method of treating cancer comprising the step of co-administering to a subject in need thereof an effective amount of a compound of claim 1 or a pharmaceutically acceptable salt thereof; and a second therapeutic agent selected from an immunotherapy agent and a therapeutic antibody.

27. The method of claim 26, wherein the immunotherapy agent is a checkpoint inhibitor.

28. The method of claim 26, wherein the therapeutic antibody is selected from an antibody selective for EGFR and an antibody selective for Her 2.

* * * * *